US010829744B2

(12) United States Patent
Rhee et al.

(10) Patent No.: US 10,829,744 B2
(45) Date of Patent: Nov. 10, 2020

(54) MICROORGANISM HAVING ENHANCED CELLULOSE SYNTHASE GENE STABILITY AND METHOD OF PRODUCING CELLULOSE BY USING THE SAME

(71) Applicants: Samsung Electronics Co., Ltd., Suwon-si (KR); Korea Advanced Institute of Science and Technology, Daejeon (KR)

(72) Inventors: Hongsoon Rhee, Suwon-si (KR); Kijun Jeong, Daejeon (KR); Jaehyung Lee, Daejeon (KR); Jinhwan Park, Suwon-si (KR); Donghoon Hur, Daejeon (KR)

(73) Assignees: Samsung Electronics Co., Ltd. (KR); Korea Advanced Institute of Science and Technology (KR)

( * ) Notice: Subject to any disclaimer, the term of this patent is extended or adjusted under 35 U.S.C. 154(b) by 0 days.

(21) Appl. No.: 16/224,427

(22) Filed: Dec. 18, 2018

(65) Prior Publication Data

US 2019/0185827 A1 Jun. 20, 2019

(30) Foreign Application Priority Data

Dec. 18, 2017 (KR) ........................ 10-2017-0174358

(51) Int. Cl.

| | |
|---|---|
| ***C12N 9/10*** | (2006.01) |
| ***C12P 19/04*** | (2006.01) |
| ***C07K 14/195*** | (2006.01) |
| ***C12P 19/18*** | (2006.01) |

(52) U.S. Cl.

CPC .......... *C12N 9/1059* (2013.01); *C07K 14/195* (2013.01); *C12P 19/04* (2013.01); *C12P 19/18* (2013.01); *C12Y 204/01012* (2013.01)

(58) Field of Classification Search

CPC ........ C07K 14/195; C12P 19/04; C12P 19/18; C12Y 204/01012; C12N 9/1059

See application file for complete search history.

(56) References Cited

U.S. PATENT DOCUMENTS

| | | | |
|---|---|---|---|
| 5,268,274 | A | 12/1993 | Ben-Bassat et al. |
| 8,119,365 | B2 | 2/2012 | Blattner et al. |
| 8,658,399 | B2 | 2/2014 | Kim et al. |
| 8,679,779 | B2 | 3/2014 | Bayon et al. |
| 2011/0262696 | A1 | 10/2011 | Bayon et al. |
| 2013/0011385 | A1 | 1/2013 | Li et al. |
| 2016/0244796 | A1 | 8/2016 | Zimmer et al. |

FOREIGN PATENT DOCUMENTS

| | | |
|---|---|---|
| JP | H11-127867 A | 5/1999 |

OTHER PUBLICATIONS

Siguier et al., Bacterial insertion sequence: their genomic impact and diversity. FEMS Microbiol Rev., 201, vol. 38: 865-891, (Year: 2014).*

Vandecraen et al., The impact of insertion sequences on bacterial genome plasticity and adaptability. Critical Rev Microbiol., 2017, vol. 43(6): 709-730. (Year: 2017).*

Zhang et al., Complete genome sequence of the cellulose-producing strain Komagataeibacter nataicola RZS01. Nature Scientific Reports, 2017, vol. 7:4431, 8 pages (Year: 2017).*

Coucheron et al., "An *Acetobacter xylinum* Insertion Sequence Element Associated with Inactivation of Cellulose Production", *Journal of Bacteriology*, 173(18): 5723-5731 (1991).

Matsutani et al., "Adaptive mutation related to cellulose producibility in *Komagataeibacter medellinensis* (*Gluconacetobacter xylinus*) NBRC 3288", *Appl. Microbiol. Biotechnol.*, 99:7229-7240 (2015).

Valera et al., "Cellulose production and cellulose synthase gene detection in acetic acid bacteria", *Appl. Microbiol. And Biotechnol.*, 99(3): 1349-1361 (2014).

Wagner et al., "A survey of bacterial insertion sequences using IScan", *Nucleic Acids Research*, 35(16): 5284-5293 (2007).

European Patent Office, extended European search report in European Patent Application No. 18212740.7 (dated Feb. 20, 2019).

Rune Standal et al., "A New Gene Required for Cellulose Production and a Gene Encoding Cellulolytic Activity in *Acetobacter xylinum* Are Colocalized with the bcs Operon," *Journal of Bacteriology*, vol. 176(3), p. 665-672 (1994).

Hideto Takami et al., "Identification and Distribution of New Insertion Sequences in the Genome of Alkaliphilic *Bacillus halodurans* C-125," *Journal of Bacteriology*, 183(14), p. 4345-4356 (2001).

* cited by examiner

*Primary Examiner* — Ganapathirama Raghu

(74) *Attorney, Agent, or Firm* — Leydig, Voit & Mayer, Ltd.

(57) ABSTRACT

Provided is a recombinant microorganism having enhanced cellulose synthase gene stability, a method of producing cellulose by using the recombinant microorganism, and a method of preparing the recombinant microorganism.

15 Claims, 3 Drawing Sheets

Specification includes a Sequence Listing.

MICROORGANISM HAVING ENHANCED CELLULOSE SYNTHASE GENE STABILITY AND METHOD OF PRODUCING CELLULOSE BY USING THE SAME

CROSS-REFERENCE TO RELATED APPLICATION

This application claims the benefit of Korean Patent Application No. 10-2017-0174358, filed on Dec. 18, 2017, in the Korean Intellectual Property Office, the entire disclosure of which is hereby incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 62,190 Byte ASCII (Text) file named “740201_ST25.TXT,” created on Dec. 18, 2018.

BACKGROUND

1. Field

The present disclosure relates to a recombinant microorganism having enhanced cellulose synthase gene stability, a method of producing cellulose by using the recombinant microorganism, and a method of preparing the microorganism.

2. Description of the Related Art

Studies examining microbial cellulose production have largely focused on fermentation of acetic acid bacteria, which naturally produce cellulose. Acetic acid bacteria utilize sugars to produce UDP-glucose, which is a cellulose precursor. UDP-glucose is converted into cellulose by cellulose synthase. However, under shaking culture, wild-type strains of acetic acid bacteria often mutate into $Cel^{-}$ strains that lose the ability to produce cellulose. This spontaneous mutation therefore decreases the efficiency of cellulose production by such microorganisms.

Accordingly, there is a need to develop a cellulose-producing microorganism that stably maintains its ability to produce cellulose during culture.

SUMMARY

Provided is a modified microorganism in which the ability to produce cellulose is stabilized relative to a wild-type microorganism, wherein the modified microorganism comprises a genetic modification that inactivates an insertion sequence (IS) recognition site in a gene encoding cellulose synthase A.

Other aspects of the disclosure provide a method of preparing the modified microorganism, and a method of producing cellulose by using the microorganism.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1A:
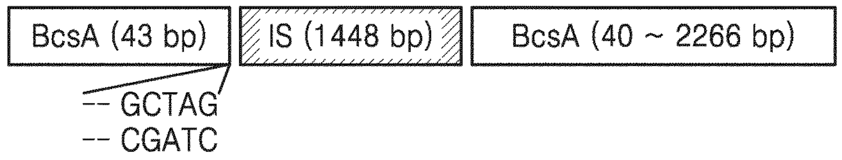
FIG. 1A illustrates cellulose synthase A gene, in which an insertion sequence (IS) element is inserted into a recognition site.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term “and/or” includes any and all combinations of one or more of the associated listed items.

In the present disclosure, a recognition site for an insertion sequence (IS) is a site or sequence in a gene into which an insertion sequence (IS) element is inserted, typically by a transposase enzyme. For ease of reference the recognition site will sometimes be referred to herein as an IS recognition site.

The term “insertion sequence element” refers to a polynucleotide having a nucleotide sequence that is inserted into the genome of a host cell at the recognition site. The polynucleotide may be DNA. The insertion sequence element may include a transposition-related gene and a terminal inverted repeat sequence. The gene may be a gene encoding transposase. The insertion sequence element may include a transposon.

In the present disclosure, the term “transposase” refers to an enzyme that catalyzes an insertion reaction of a gene.

Inactivation of an IS recognition site means that the IS recognition site is modified and, as a result, either the insertion frequency of the insertion sequence element at the IS recognition site is lowered or the insertion sequence element is not inserted at all.

The term “gene”, as used herein, refers to a nucleic acid sequence that encodes and expresses a specific protein. In some embodiments, a gene may include a regulatory sequence of a 5'-non-coding sequence and/or a 3'-non-coding sequence.

A “sequence identity” of a polynucleotide (nucleic acid) or a polypeptide, as used herein, refers to a degree of identity between nucleotide bases or amino acid residues of aligned sequences over a particular region. The sequence identity is a value that is obtained by comparing two sequences in certain comparable regions via optimal alignment of the two sequences. A percentage of sequence identity may be calculated by, for example, comparing two optimally aligned sequences in the entire comparable region, determining the number of locations where the two sequences have an identical amino acid or identical nucleic acid, dividing the number of matching locations by the total number of locations in the comparable region (e.g., the range size), and multiplying the result by 100 to obtain the percentage of the sequence identity. The percentage of the sequence identity may be determined using a known sequence comparison program, for example, BLASTN (NCBI), BLASTP (NCBI), CLC Main Workbench (CLC bio), MegAlign™ (DNASTAR Inc), etc.

The term "genetic modification", as used herein, refers to an artificial alteration in the constitution or structure of the genetic material of a cell. The "genetic modification" may be completed by site-directed mutagenesis or homologous recombination.

The term "parent cell", as used herein, refers to an original cell, for example, a non-genetically engineered cell of the same type as an engineered microorganism. With respect to a particular genetic modification, the "parent cell" may be a cell that lacks the particular genetic modification, but is identical in all other aspects to the cell with the genetic modification.

One aspect of the present invention provides a recombinant microorganism having an ability to produce cellulose, the microorganism including a genetic modification that inactivates a recognition site into which an insertion sequence (IS) element may be inserted.

The insertion sequence element may include a nucleotide sequence encoding transposase having about 80% or more, about 85% or more, about 90% or more, about 95% or more, about 97% or more, about 98% or more, about 99% or more, or about 100% sequence identity to the amino acid sequence of SEQ ID NO: 3. The amino acid sequence of SEQ ID NO: 3 may be an amino acid sequence of transposase that exists in an insertion sequence element isolated from *Komagataeibacter xylinus*. The insertion sequence element may belong to the IS1182 family or IS5 family. The IS5 family may belong to the IS5 subgroup. The IS1182 family and IS5 family may have the characteristics set out in Table 1. The insertion sequence element may have about 80% or more, about 85% or more, about 90% or more, about 95% or more, about 97% or more, about 98% or more, about 99% or more, or about 100% sequence identity to the nucleotide sequence of SEQ ID NO: 1.

TABLE 1

| Family | Subgroup | General size range | DR | Terminal | IR | ORF | frame shift | Chemical |
|---|---|---|---|---|---|---|---|---|
| IS1182 | | 1330-1950 | 0-60 | | Y | 1 | | DDE |
| IS5 | IS903 | 950-1150 | 9 | GG | Y | 1 | | DDE |
| | ISL2 | 850-1200 | 2-3 | | | 1 | | |
| | ISH1 | 900-1150 | 8 | -GC | | 1 | | |
| | IS5 | 1000-1500 | 4 | Ga/g | | 1 | | |
| | IS427 | 800-1000 | 2-4 | Ga/g | | 2 | ORFAB | |

In Table 1, the "General size range" column refers to the general number of base pairs (bp) in each group. The abbreviation "DR" refers to the number of direct target repeats expressed as base pair. The "Terminal" column refers to the conserved terminal base pairs. In this column, capital letters represent the most frequently conserved bases. Small letters separated by a slash (e.g., a/g) indicate alternative conservation at that location. The "IR" column represents the presence (Y) or absence (N) of terminal inverted repeats. The "ORF" column refers to the number of open reading frames. The "frame shift" denotes any frame shift mutations. The "DDE" in the "Chemical" column represents the common acidic triad (i.e., Asp, Asp, Glu) presumed to be part of the active site of transposase.

The recognition site may exist in a nucleotide sequence encoding an amino acid sequence (e.g., SEQ ID NO: 4) of cellulose synthase A. The recognition site may have a nucleotide sequence of GCTAGA. The genetic modification may be a nucleotide substitution of one or more nucleotides in the sequence of the recognition site that does not result in the modification of the encoded amino acid sequence. In one embodiment, The genetic modification may be modification of a nucleotide sequence, i.e., a nucleotide sequence corresponding to positions 37-45 of SEQ ID NO: 26, while maintaining the RLD amino acid sequence at positions 13 to 15 of SEQ ID NO: 4, e.g., the amino acid sequence of cellulose synthase A. In another embodiment, the genetic modification may be a modification of a nucleotide sequence, i.e., a nucleotide sequence corresponding to positions 37-42 of SEQ ID NO: 26, while maintaining the RL amino acid sequence at positions 13 to 14 of SEQ ID NO:4. The genetic modification may be substitution in SEQ ID NO: 26 of AGA, CGT, CGC, CGA, or CGG for AGG encoding R at positions 37 to 39, and/or CTT, CTC, CTG, TTT, TTC, TTA, or TTG for CTA encoding L at positions 40 to 42, and/or GAT for GAC encoding D at positions 43 to 45 in the nucleotide sequence encoding cellulose synthase A of SEQ ID NO: 26.

In a further embodiment, the genetic modification may be a substitution of ATTGGA for GCTAGA in the nucleotide sequence encoding cellulose synthase A of SEQ ID NO: 26, which yields SEQ ID NO: 5.

The microorganism may belong to any one of the genus *Acetobacter*, the genus *Gluconacetobacter*, and the genus *Komagataeibacter*. The microorganism may be *K. xylinus* (also called "*G. xylinus*"), *K. rhaeticus, K. swingsii, K. kombuchae, K. nataicola*, or *K. sucrofermentans.*

Another aspect of the disclosure provides a method of producing cellulose, the method including culturing the recombinant microorganism in a medium to produce cellulose in a culture; and collecting the cellulose from the culture. The recombinant microorganism used in this method of producing cellulose is the same as described above.

The culturing may be appropriately controlled for the production of cellulose. The culturing may be performed under aerobic conditions for cell proliferation. The culturing may be performed by shaking culture or static culture without shaking. A density of the microorganism may be a density which gives enough space so as not to disturb production of cellulose.

The medium may comprise elements selected from carbon sources, nitrogen sources, salts, trace elements, and combinations thereof. The carbon source may include monosaccharides, disaccharides, or polysaccharides. The carbon source may include glucose, fructose, mannose, or galactose as an assimilable sugar. The nitrogen source may be an organic nitrogen compound or an inorganic nitrogen compound. The nitrogen source may be amino acids, amides, amines, nitrates, or ammonium salts.

An oxygen condition for culturing the microorganism may be an aerobic condition of a normal oxygen partial pressure. A normal oxygen partial pressure refers to oxygen partial pressure when the medium is in equilibrium with an atmospheric air.

The medium may be any common medium suitable for cell growth, such as a minimal or complex medium containing appropriate supplements. The suitable medium may be available from commercial suppliers or may be prepared according to known preparation methods.

The medium may include ethanol or cellulose. The ethanol may be about 0.1% (v/v) to about 5% (v/v), for example, about 0.3% (v/v) to about 2.5% (v/v), about 0.3% (v/v) to about 2.0% (v/v), about 0.3% (v/v) to about 1.5% (v/v), about 0.3% (v/v) to about 1.25% (v/v), about 0.3% (v/v) to about 1.0% (v/v), about 0.3% (v/v) to about 0.7% (v/v), or about 0.5% (v/v) to about 3.0% (v/v) with respect to a volume of the medium. The cellulose may be about 0.5% (v/v) to about 5% (w/v), about 0.5% (v/v) to about 2.5% (w/v), about 0.5% (v/v) to about 1.5% (w/v), or about 0.7% (v/v) to about 1.25% (w/v) with respect to a weight of the medium. The cellulose may be carboxylated cellulose. The carboxylated cellulose may be carboxymethyl cellulose ("CMC"). The CMC may be sodium CMC.

The culturing may be performed at 25° C. to 37° C., 27° C. to 35° C., or 29° C. to 33° C.

The method may include collecting cellulose from the culture. The separating may be, for example, collecting of a cellulose pellicle which is formed on the top of the medium. The cellulose pellicle may be collected by physically stripping off the cellulose pellicle or by removing the medium. In some embodiments, the separated pellicle maintains its shape without damage.

Still another aspect provides a method of preparing a microorganism having a stabilized ability to produce cellulose, the method including introducing the genetic modification into the microorganism having the ability to produce cellulose, wherein the genetic modification inactivates a recognition site into which an insertion sequence (IS) element is inserted.

In the method, the genetic modification may include manipulation of the nucleotide sequence of the recognition site. The manipulation may be substitution of nucleotides. The genetic modification may be performed by a known method, such as site-directed mutagenesis, etc.

The phrase "microorganism having stabilized the ability to produce cellulose" indicates that when cells are cultured, the rate of conversion of the cells into cellulose non-producing cells is lower than that of parent cells. In this regard, the culture may be performed for a period of time to allow the cells to divide for a predetermined number of division. The number of division may be 5 times, 10 times, 50 times, 100 times, 500 times, 1000 times, or 5000 times. The cellulose non-producing cells may not express cellulose synthase A or may express cellulose synthase A with reduced activity or without activity.

In one aspect of the present invention, culturing a microorganism having an ability to produce cellulose including a genetic modification that inactivates a recognition site into which an insertion sequence (IS) element may be inserted reduces the occurrence of a cellulose non-producing mutant strain during culture.

The method of producing cellulose according to an aspect of the present invention may be used to efficiently produce cellulose.

In another embodiment of the present invention, a method of preparing a microorganism having a stabilized ability to produce cellulose may be used to efficiently prepare the microorganism having the stabilized ability to produce cellulose.

Hereinafter, the present disclosure will be described in more detail with reference to Examples. However, these Examples are for illustrative purposes only, and the scope of the present disclosure is not intended to be limited by these Examples.

Example 1: Culture of Transformed Microorganism Having Modified IS Insertion Site and Cellulose Synthase Gene Stability Thereof In this Example, an IS insertion site was inactivated in cellulose synthase A gene of *Komagataeibacter xylinus* (Korean Culture Center of Microorganisms KCCM 41431). Thereafter, the microorganism having the IS insertion site-inactivated cellulose synthase A gene was cultured and proliferated, and stability of the cellulose synthase A gene and an ability to produce cellulose were examined.

In detail, ATTGGA was substituted for GCTAGA corresponding to nucleotides at positions 39 to 43 of SEQ ID NO: 26, which encodes cellulose synthase A in a *K. xylinus* cell.

The substitution was performed by crossover recombination of genome. A pUC19_bcsA_m vector was used in this crossover recombination. The pUC19_bcsA_m vector includes an upper arm and a lower arm, which are homologous sequences to the genome of *K. xylinus*. Namely, the pUC19_bcsA_m vector includes (1) a homologous sequence (SEQ ID NO: 6) of 776 bp from a start codon to (−)776 bp in open reading frame of cellulose synthase A, and (2) a homologous sequence (SEQ ID NO: 7) of 908 bp from a start codon to (+)908 bp in open reading frame of cellulose synthase A. A chloramphenicol resistance gene, which is a selection marker, and a gapA promoter, which ensures transcription of cellulose synthase A, were inserted between the two homologous sequences (i.e., SEQ ID NOs. 6 and 7). A PCR fragment of the upper arm was obtained by using the genome of *K. xylinus* as a template and an upper arm_F/R primer set (SEQ ID NOS: 8 and 9), and a PCR fragment of the lower arm was obtained by using the genome of *K. xylinus* as a template and a lower arm_F/R primer set (SEQ ID NOS: 10 and 11). A PCR fragment of the chloramphenicol resistance gene was obtained by using a pTsaP vector (SEQ ID NO: 12) as a template and Ptac_F/R (SEQ ID NOS: 13 and 14) and Cat_F/R (SEQ ID NOS: 15 and 16) primer sets. A PCR fragment of the gapA promoter was obtained by using a pTsa_EX2 vector (SEQ ID NO: 17) as a template and a PgapA_F/R (SEQ ID NOS: 18 and 19) primer set. The obtained PCR fragments were cloned into EcoR1 and HindIII restriction sites of a pUC19 vector (# N3041S, NEB) using an IN-FUSION® HD cloning kit (# PT5162-1, Clonetech) to prepare a pUC19_bcsA vector (SEQ ID NO: 20). For sequence modification of the IS insertion site, pUC19_bcsA_m (SEQ ID NO: 23) was constructed, based on the pUC19_bcsA vector, by using a bcsA_m_F/R (SEQ ID NOS: 21 and 22) primer set according to the description of a QuikChange® II Site-Directed Mutagenesis Kit (Agilent Technology, USA).

Next, the pUC19_bcsA_m vector was introduced into *K. xylinum* cells by electroporation. Thereafter, the cells were cultured on a plate, on which an HS medium containing 1.5% w/v bacto agar with 100 mg/L of chloramphenicol was spread, at 30° C. to allow homologous recombination, and a microorganism into which the substituted gene was introduced was selected. In order to examine whether the substituted gene was introduced into the selected microorganism, genotyping was performed by sequencing of a PCR product obtained by using bcsA_F and bcsA_R primers (SEQ ID NOS: 24 and 25).

Next, the prepared recombinant strain (hereinafter, also referred to as 'Koma-IS') and a wild-type strain were seeded in a 125 ml flask containing 25 ml of Hestrin Schramm (HS) medium (0.5% peptone, 0.5% yeast extract, 0.27% $Na_2HPO_4$, 0.15% citric acid, and 4% glucose), respectively and cultured under shaking at 30° C. and 230 rpm, followed by subculturing every other day. Each of the 24 colonies from the recombinant strain and the wild-type strain were seeded and cultured in one flask, respectively. The presence of a cellulose non-producing mutant strain (hereinafter, also referred to as '$Cel^-$ strain') in each of the cultures was examined by phenotyping and genotyping.

Figure 1B:
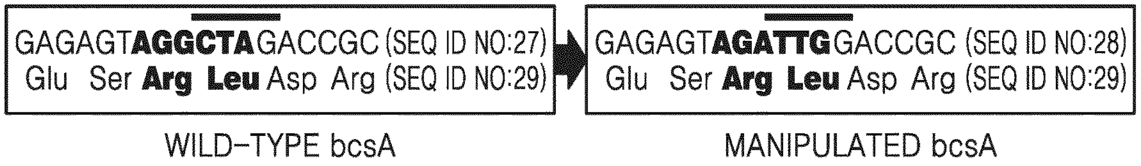
FIG. 1B illustrates modification of the insertion sequence (IS) recognition site.

FIG. 1A illustrates cellulose synthase A gene, in which the insertion sequence (IS) element was inserted into the recognition site. FIG. 1B illustrates the genetic modification of the recognition site.

Figure 2A:
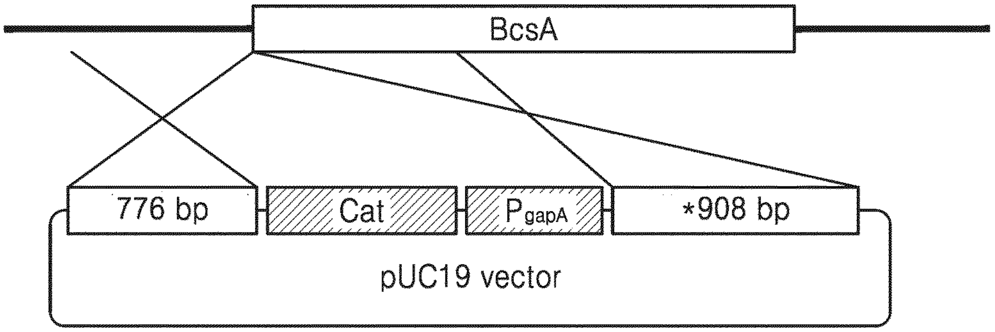
FIG. 2A illustrates a vector for constructing a recombinant microorganism having an modified IS insertion site in cellulose synthase A by homologous crossover recombination.
Figure 2B:
FIG. 2B illustrates a modified genome of the recombinant microorganism.

FIG. 2A illustrates the vector for constructing the recombinant microorganism having the improved IS insertion site of cellulose synthase A by homologous crossover recombination. FIG. 2B illustrates the modified genome of the recombinant microorganism.

Figure 3:
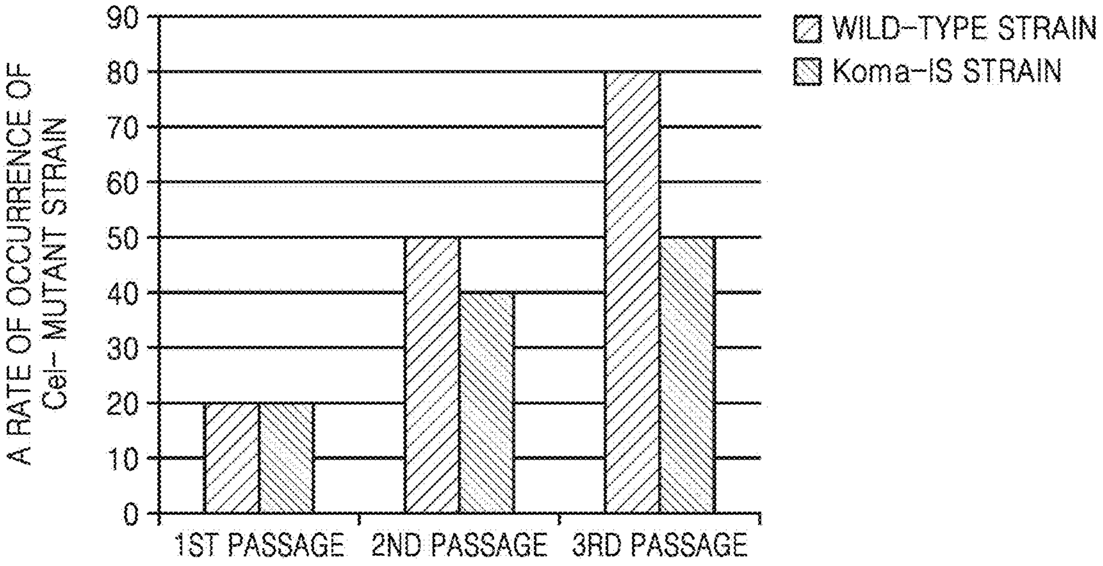
FIG. 3 shows a rate of occurrence of a cellulose non-producing mutant strain according to the number of cell passages.

FIG. 3 shows a rate of occurrence of the cellulose non-producing mutant strain according to the number of cell passages. In FIG. 3, the rate of occurrence of the cellulose non-producing mutant strain is a percentage obtained by dividing the number of flasks containing a cellulose non-producing mutant strain (confirmed by phenotyping) by the total number of culture flasks, at each passage. As shown in FIG. 3, the rate of occurrence of the $Cel^-$ mutant of the recombinant strain was 50% after third subculturing, which was significantly lower than 80% produced by the wild-type strain.

Figure 4:
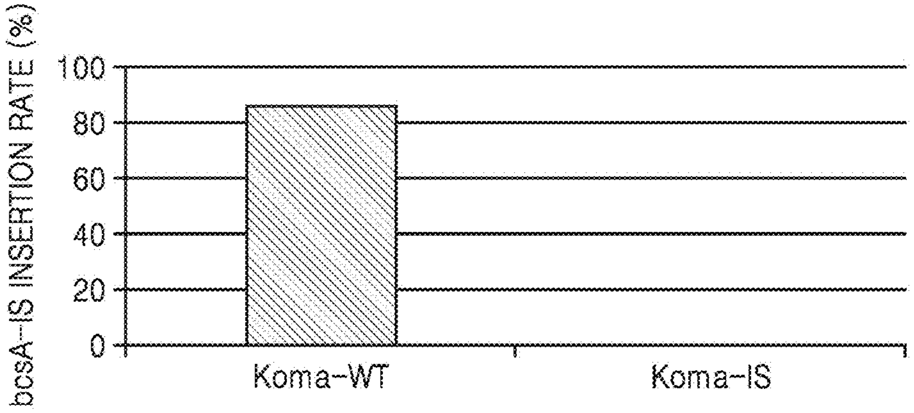
FIG. 4 shows a rate of occurrence of the cellulose non-producing mutant strain after a third subculture.

FIG. 4 shows a rate of occurrence of the cellulose non-producing mutant strain after third subculturing. In FIG. 4, the rate of occurrence of the cellulose non-producing mutant strain is a percentage obtained by dividing the number of flasks in which occurrence of the cellulose non-producing mutant strain was confirmed by genotyping by the total number of culture flasks, after subculturing. As shown in FIG. 4, the wild-type strain showed 87.5% of the rate of occurrence of the cellulose non-producing mutant strain, whereas the recombinant strain showed no occurrence of the cellulose non-producing mutant strain. The genotyping was performed by sequencing of PCR products obtained by using bcsA_F and bcsA_R primers (SEQ ID NOS: 24 and 25). The genotyping showed that an IS sequence of 1448 bp was inserted after the nucleotide sequence encoding BcsA of 43 bp, and there were GCTAG repeats at both ends thereof (see FIG. 1A). After insertion of the sequence, the 40-43th nucleotides (CTAG) of bcsA were replicated as a duplication region of the insertion sequence.

Referring to FIGS. 3 and 4, the percentage of the cellulose non-producing mutant strain confirmed by phenotyping (FIG. 3) was higher than the percentage of the cellulose non-producing mutant strain confirmed by genotyping (FIG. 4), indicating that occurrence of the cellulose non-producing mutant strain may be caused by a culture method as well as genetic factors.

Figure 5:
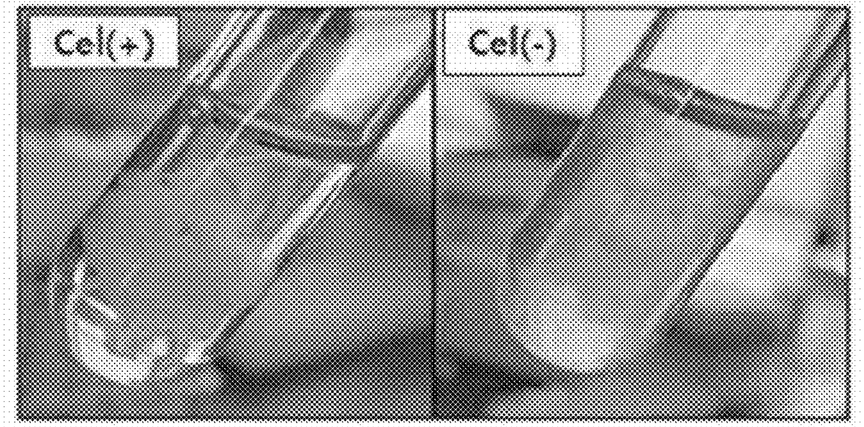
FIG. 5 is a photograph showing cultures of Cel+ and Cel− strains.

FIG. 5 is a photograph showing cultures of Cel+ and Cel− strains. As shown in FIG. 5, Cel− strain showed a small amount of cellulose but a high growth rate, as compared with Cel+ strain.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A modified microorganism in which the ability to produce cellulose is stabilized relative to a wild-type microorganism, the modified microorganism comprising a gene encoding cellulose synthase A with a genetic modification that inactivates an insertion sequence (IS) recognition site in the gene encoding cellulose synthase A, wherein the IS recognition site prior to the genetic modification comprises the nucleotide sequence GCTAGA, and the genetic modification is a substitution of one or more nucleotides of the IS recognition site without modification of an amino acid sequence encoded by the polynucleotide sequence comprising the IS recognition site, wherein the microorganism is *Komagataeibacter*.

2. The microorganism of claim 1, wherein the genetic modification is substitution of ATTGGA for GCTAGA.

3. The microorganism of claim 1, wherein the IS recognition site is for an insertion sequence element comprising a nucleotide sequence encoding a transposase having 80% or more sequence identity to the amino acid sequence of SEQ ID NO: 3.

4. The microorganism of claim 1, wherein the IS recognition site is for an insertion sequence element that belongs to the IS1182 family or IS5 family of insertion sequence elements.

5. The microorganism of claim 1, wherein the IS recognition site is for an insertion sequence element that has 90% or more sequence identity to the polynucleotide sequence of SEQ ID NO: 1.

6. The microorganism of claim 1, wherein the microorganism is *Komagataeibacter xylinus*.

7. A method of producing cellulose, the method comprising:

culturing the microorganism of claim 1 in a medium to produce cellulose in a culture; and collecting cellulose from the culture.

8. The method of claim 7, wherein the genetic modification is substitution of ATTGGA for GCTAGA.

9. The method of claim 7, wherein the IS recognition site is for an insertion sequence element that comprises a nucleotide sequence encoding a transposase having 80% or more sequence identity to the amino acid sequence of SEQ ID NO: 3.

10. The method of claim 7, wherein the IS recognition site is for an insertion sequence element that belongs to the IS1182 family or IS5 family of insertion sequence elements.

11. The method of claim 7, wherein the IS recognition site is for an insertion sequence element that has 90% or more sequence identity to the polynucleotide sequence of SEQ ID NO: 1.

12. A method of preparing a modified microorganism of claim 1, the method comprising introducing a genetic modification into a microorganism having an ability to produce cellulose, wherein the genetic modification inactivates an IS recognition site in a gene encoding cellulose synthase A, wherein the IS recognition site prior to the genetic modification comprises the nucleotide sequence GCTAGA, and the genetic modification is a substitution of one or more nucleotides of the IS recognition site without modification of an amino acid sequence encoded by the polynucleotide sequence comprising the IS recognition site, wherein the microorganism is *Komagataeibacter*.

13. A modified microorganism comprising a cellulose synthase A gene comprising SEQ ID NO: 26 in which one or more nucleotides of the nucleotide sequence corresponding to positions 37-45 of SEQ ID NO: 26 have been substituted.

14. The modified microorganism of claim 13, wherein the substitution comprises:

(a) substitution in the sequence AGG at positions 37 to 39 of SEQ ID NO: 26 to provide the sequence AGA, CGT, CGC, CGA, or CGG;

(b) substitution in the sequence CTA at positions 40 to 42 of SEQ ID NO: 26 to provide the sequence CTT, CTC, CTG, TTT, TTC, TTA, or TTG; and/or (c) substitution in the sequence GAC at positions 43 to 45 of SEQ ID NO: 26 to provide the sequence GAT.

15. A modified microorganism comprising a cellulose synthase A gene comprising SEQ ID NO: 5.

* * * * *

SEQUENCE LISTING

```
<160> NUMBER OF SEQ ID NOS: 29

<210> SEQ ID NO 1
```

-continued

```
<211> LENGTH: 1450
<212> TYPE: DNA
<213> ORGANISM: Komagataeibacter xylinus

<400> SEQUENCE: 1

cagcctgtcg ggttgggcat tttgcggctg ataacgccga ggctgacccg gcttatgctg     60

cgtgaagccg tgccattctt ttgcagttgt atgcgagagc gacgagtgtc cattcggtcg    120

tgacttttgg aaggccacgc agactgaatc ttctgaagcc catgatgctt ttgataattc    180

caaagaccgg ttcaacggtc tgttttcgta gtctgtaaat atttccggct tttgtggttt    240

ccagtttttt cttcatggcg agccgccagg gttcggttat ccggcgtggc tcctttgctt    300

cgggatgggg tcggaagtcg taaggtctgc gggcacaggg ccgtccaatg gcgaccagcg    360

gatcaatgcc cttttcctgc agtttccgga ccgcctgtcc gctggcgtaa ccggtgtcgg    420

caagcacctt ctccgggaga ccgattgtgt gttccatcga cagcaccgtg tcggcaaagg    480

atggcgcatc cgctgacgtg gcgacaacgc cggttgtcac gatcagctgg ctgccttcgg    540

cgcagactac ggcctgggca ttgtaagcct gccggaactc gtgagcgtcc gaacgccgca    600

tgaggcggct gtcgggatcg gtcaggctga tctgccggtc gggtggcggt tcatcatccg    660

gcggtttcgg cgccctgcca cgacgccctg tttttgcgtc atacaccgcc ttcttttttct    720

cgtatgccgg tcgcgccgcc tcggcctgcg ccttcgcatc tgcttccagc cgggcgcagg    780

cttcatccag cttcgctttc agcgcttccc ggcgggcaag ttcttccggc aatgcctgcg    840

gatcactgtc tgtggcatct gcgtgctccg cctggtccat cagtttcgcg atatccaccg    900

ccagctgttc gcgcagcgcc ctgatccggt catagcgcac cgaacggtat ttcgatgcgt    960

cagcatcgat tttcgtgccg tcgatcgaca ccacgcccag acgcagcagg cctgtctcgc   1020

gcgccagaag caggacctgt gcaaatgcag cttcaatggc gcccctgttc gtccggcgga   1080

aggtcgcaat cgtatcatga tccggatgca ggttcgccgc cacgaagcgc accccgatgt   1140

cgcgatatgt cgcccgctcg atccggcgtg aggaaaacaa cccgttcgca tagctgaaga   1200

tcagaagggc cagcatcaga cgcggatggt actgtgcctt gccacccgtg cgcactggca   1260

cgcagaacgc actcatcgga acccgctcaa cggctgcgac aatgaaatgc gccatatcgt   1320

cagcaggaag ccacgacttc agatcaggcg gcagaagata cggctgagac cggtcaaacg   1380

ggatgaagct gctcatctca ccaccttaca accttacccc ttcactgggt accccaaccc   1440

gacaggctgc                                                          1450


<210> SEQ ID NO 2
<211> LENGTH: 1396
<212> TYPE: PRT
<213> ORGANISM: Komagataeibacter xylinus

<400> SEQUENCE: 2

Cys Ala Gly Cys Cys Thr Gly Thr Cys Gly Gly Gly Thr Thr Gly Gly
1               5                   10                  15

Gly Cys Ala Thr Thr Thr Thr Gly Cys Gly Gly Cys Thr Gly Ala Thr
            20                  25                  30

Ala Ala Cys Gly Cys Cys Gly Ala Gly Gly Cys Thr Gly Ala Cys Cys
        35                  40                  45

Cys Gly Gly Cys Thr Thr Ala Thr Gly Cys Thr Gly Cys Gly Thr Gly
    50                  55                  60

Ala Ala Gly Cys Cys Gly Thr Gly Cys Cys Ala Thr Thr Cys Thr Thr
65                  70                  75                  80
```

-continued

```
Thr Thr Gly Cys Ala Gly Thr Thr Gly Thr Ala Thr Gly Cys Gly Ala
                85                  90                  95

Gly Ala Gly Cys Gly Ala Cys Gly Ala Gly Thr Gly Thr Cys Cys Ala
            100                 105                 110

Thr Thr Cys Gly Gly Thr Cys Gly Thr Gly Ala Cys Thr Thr Thr Thr
        115                 120                 125

Gly Gly Ala Ala Gly Gly Cys Cys Ala Cys Gly Cys Ala Gly Ala Cys
    130                 135                 140

Thr Gly Ala Ala Thr Cys Thr Thr Cys Thr Gly Ala Ala Gly Cys Cys
145                 150                 155                 160

Cys Ala Thr Gly Ala Thr Gly Cys Thr Thr Thr Thr Gly Ala Thr Ala
                165                 170                 175

Ala Thr Thr Cys Cys Ala Ala Ala Gly Ala Cys Cys Gly Gly Thr Thr
            180                 185                 190

Cys Ala Ala Cys Gly Gly Thr Cys Thr Gly Thr Thr Thr Thr Cys Gly
        195                 200                 205

Thr Ala Gly Thr Cys Thr Gly Thr Ala Ala Ala Thr Ala Thr Thr Thr
    210                 215                 220

Cys Cys Gly Gly Cys Thr Thr Thr Thr Gly Thr Gly Gly Thr Thr Thr
225                 230                 235                 240

Cys Cys Ala Gly Thr Thr Thr Thr Thr Thr Cys Thr Thr Cys Ala Thr
                245                 250                 255

Gly Gly Cys Gly Ala Gly Cys Cys Gly Cys Cys Ala Gly Gly Gly Thr
            260                 265                 270

Thr Cys Gly Gly Thr Thr Ala Thr Cys Cys Gly Gly Cys Gly Thr Gly
        275                 280                 285

Gly Cys Thr Cys Cys Thr Thr Thr Gly Cys Thr Thr Cys Gly Gly Gly
    290                 295                 300

Ala Thr Gly Gly Gly Gly Thr Cys Gly Gly Ala Ala Gly Thr Cys Gly
305                 310                 315                 320

Thr Ala Ala Gly Gly Thr Cys Thr Gly Cys Gly Gly Gly Cys Ala Cys
                325                 330                 335

Ala Gly Gly Gly Cys Cys Gly Thr Cys Cys Ala Ala Thr Gly Gly Cys
            340                 345                 350

Gly Ala Cys Cys Ala Gly Cys Gly Gly Ala Thr Cys Ala Ala Thr Gly
        355                 360                 365

Cys Cys Cys Thr Thr Thr Thr Cys Cys Thr Gly Cys Ala Gly Thr Thr
    370                 375                 380

Thr Cys Cys Gly Gly Ala Cys Cys Gly Cys Cys Thr Gly Thr Cys Cys
385                 390                 395                 400

Gly Cys Thr Gly Gly Cys Gly Thr Ala Ala Cys Cys Gly Gly Thr Gly
                405                 410                 415

Thr Cys Gly Gly Cys Ala Ala Gly Cys Ala Cys Cys Thr Thr Cys Thr
            420                 425                 430

Cys Cys Gly Gly Gly Ala Gly Ala Cys Cys Gly Ala Thr Thr Gly Thr
        435                 440                 445

Gly Thr Gly Thr Thr Cys Cys Ala Thr Cys Gly Ala Cys Ala Gly Cys
    450                 455                 460

Ala Cys Cys Gly Thr Gly Thr Cys Gly Gly Cys Ala Ala Ala Gly Gly
465                 470                 475                 480

Ala Thr Gly Gly Cys Gly Cys Ala Thr Cys Cys Gly Cys Thr Gly Ala
                485                 490                 495

Cys Gly Thr Gly Gly Cys Gly Ala Cys Ala Ala Cys Gly Cys Cys Gly
```

-continued

```
            500                 505                 510

Gly Thr Thr Gly Thr Cys Ala Cys Gly Ala Thr Cys Ala Gly Cys Thr
        515                 520                 525

Gly Gly Cys Thr Gly Cys Cys Thr Thr Cys Gly Gly Cys Gly Cys Ala
    530                 535                 540

Gly Ala Cys Thr Ala Cys Gly Gly Cys Cys Thr Gly Gly Gly Cys Ala
545                 550                 555                 560

Thr Thr Gly Thr Ala Ala Gly Cys Cys Thr Gly Cys Cys Gly Gly Ala
                565                 570                 575

Ala Cys Thr Cys Gly Thr Gly Ala Gly Cys Gly Thr Cys Cys Gly Ala
            580                 585                 590

Ala Cys Gly Cys Cys Gly Cys Ala Thr Gly Ala Gly Gly Cys Gly Gly
        595                 600                 605

Cys Thr Gly Thr Cys Gly Gly Gly Ala Thr Cys Gly Gly Thr Cys Ala
    610                 615                 620

Gly Gly Cys Thr Gly Ala Thr Cys Thr Gly Cys Cys Gly Gly Thr Cys
625                 630                 635                 640

Gly Gly Gly Thr Gly Gly Cys Gly Gly Thr Thr Cys Ala Thr Cys Ala
                645                 650                 655

Thr Cys Cys Gly Gly Cys Gly Gly Thr Thr Thr Cys Gly Gly Cys Gly
            660                 665                 670

Cys Cys Cys Thr Gly Cys Cys Ala Cys Gly Ala Cys Gly Cys Cys Cys
        675                 680                 685

Thr Gly Thr Thr Thr Thr Thr Gly Cys Gly Thr Cys Ala Thr Ala Cys
    690                 695                 700

Ala Cys Cys Gly Cys Cys Thr Thr Cys Thr Thr Thr Thr Thr Cys Thr
705                 710                 715                 720

Cys Gly Thr Ala Thr Gly Cys Cys Gly Gly Thr Cys Gly Cys Gly Cys
                725                 730                 735

Cys Gly Cys Cys Thr Cys Gly Gly Cys Cys Thr Gly Cys Gly Cys Cys
            740                 745                 750

Thr Thr Cys Gly Cys Ala Thr Cys Thr Gly Cys Thr Thr Cys Cys Ala
        755                 760                 765

Gly Cys Cys Gly Gly Gly Cys Gly Cys Ala Gly Gly Cys Thr Thr Cys
    770                 775                 780

Ala Thr Cys Cys Ala Gly Cys Thr Thr Cys Gly Cys Thr Thr Thr Cys
785                 790                 795                 800

Ala Gly Cys Gly Cys Thr Thr Cys Cys Cys Gly Gly Cys Gly Gly Gly
                805                 810                 815

Cys Ala Ala Gly Thr Thr Cys Thr Thr Cys Cys Gly Gly Cys Ala Ala
            820                 825                 830

Thr Gly Cys Cys Thr Gly Cys Gly Gly Ala Thr Cys Ala Cys Thr Gly
        835                 840                 845

Thr Cys Thr Gly Thr Gly Gly Cys Ala Thr Cys Thr Gly Cys Gly Thr
    850                 855                 860

Gly Cys Thr Cys Cys Gly Cys Cys Thr Gly Gly Thr Cys Cys Ala Thr
865                 870                 875                 880

Cys Ala Gly Thr Thr Thr Cys Gly Cys Gly Ala Thr Ala Thr Cys Cys
                885                 890                 895

Ala Cys Cys Gly Cys Cys Ala Gly Cys Thr Gly Thr Thr Cys Gly Cys
            900                 905                 910

Gly Cys Ala Gly Cys Gly Cys Cys Cys Thr Gly Ala Thr Cys Cys Gly
        915                 920                 925
```

-continued

```
Gly Thr Cys Ala Thr Ala Gly Cys Gly Cys Ala Cys Cys Gly Ala Ala
    930                 935                 940

Cys Gly Gly Thr Ala Thr Thr Thr Cys Gly Ala Thr Gly Cys Gly Thr
945                 950                 955                 960

Cys Ala Gly Cys Ala Thr Cys Gly Ala Thr Thr Thr Thr Cys Gly Thr
                965                 970                 975

Gly Cys Cys Gly Thr Cys Gly Ala Thr Cys Gly Ala Cys Ala Cys Cys
            980                 985                 990

Ala Cys Gly Cys Cys Cys Ala Gly Ala Cys Gly Cys Ala Gly Cys Ala
        995                 1000                1005

Gly Gly Cys Cys Thr Gly Thr Cys Thr Cys Gly Cys Gly Cys Gly Cys
    1010                1015                1020

Cys Ala Gly Ala Ala Gly Cys Ala Gly Gly Ala Cys Cys Thr Gly Thr
1025                1030                1035                1040

Gly Cys Ala Ala Ala Thr Gly Cys Ala Gly Cys Thr Thr Cys Ala Ala
                1045                1050                1055

Thr Gly Gly Cys Gly Cys Cys Cys Cys Thr Gly Thr Thr Cys Gly Thr
            1060                1065                1070

Cys Cys Gly Gly Cys Gly Gly Ala Ala Gly Gly Thr Cys Gly Cys Ala
        1075                1080                1085

Ala Thr Cys Gly Thr Ala Thr Cys Ala Thr Gly Ala Thr Cys Cys Gly
    1090                1095                1100

Gly Ala Thr Gly Cys Ala Gly Gly Thr Thr Cys Gly Cys Cys Gly Cys
1105                1110                1115                1120

Cys Ala Cys Gly Ala Ala Gly Cys Gly Cys Ala Cys Cys Cys Cys Gly
                1125                1130                1135

Ala Thr Gly Thr Cys Gly Cys Gly Ala Thr Ala Thr Gly Thr Cys Gly
            1140                1145                1150

Cys Cys Cys Gly Cys Thr Cys Gly Ala Thr Cys Cys Gly Gly Cys Gly
        1155                1160                1165

Thr Gly Ala Gly Gly Ala Ala Ala Ala Cys Ala Ala Cys Cys Cys Gly
    1170                1175                1180

Thr Thr Cys Gly Cys Ala Thr Ala Gly Cys Thr Gly Ala Ala Gly Ala
1185                1190                1195                1200

Thr Cys Ala Gly Ala Ala Gly Gly Gly Cys Cys Ala Gly Cys Ala Thr
                1205                1210                1215

Cys Ala Gly Ala Cys Gly Cys Gly Gly Ala Thr Gly Gly Thr Ala Cys
            1220                1225                1230

Thr Gly Thr Gly Cys Cys Thr Thr Gly Cys Cys Ala Cys Cys Cys Gly
        1235                1240                1245

Thr Gly Cys Gly Cys Ala Cys Thr Gly Gly Cys Ala Cys Gly Cys Ala
    1250                1255                1260

Gly Ala Ala Cys Gly Cys Ala Cys Thr Cys Ala Thr Cys Gly Gly Ala
1265                1270                1275                1280

Ala Cys Cys Cys Gly Cys Thr Cys Ala Ala Cys Gly Gly Cys Thr Gly
                1285                1290                1295

Cys Gly Ala Cys Ala Ala Thr Gly Ala Ala Ala Thr Gly Cys Gly Cys
            1300                1305                1310

Cys Ala Thr Ala Thr Cys Gly Thr Cys Ala Gly Cys Ala Gly Gly Ala
        1315                1320                1325

Ala Gly Cys Cys Ala Cys Gly Ala Cys Thr Thr Cys Ala Gly Ala Thr
    1330                1335                1340
```

-continued

```
Cys Ala Gly Gly Cys Gly Gly Cys Ala Gly Ala Ala Gly Ala Thr Ala
1345                1350                1355                1360

Cys Gly Gly Cys Thr Gly Ala Gly Ala Cys Cys Gly Gly Thr Cys Ala
                1365                1370                1375

Ala Ala Cys Gly Gly Gly Ala Thr Gly Ala Ala Gly Cys Thr Gly Cys
            1380                1385                1390

Thr Cys Ala Thr
        1395


<210> SEQ ID NO 3
<211> LENGTH: 447
<212> TYPE: PRT
<213> ORGANISM: Komagataeibacter xylinus

<400> SEQUENCE: 3

Met Ser Ser Phe Ile Pro Phe Asp Arg Ser Gln Pro Tyr Leu Leu Pro
1               5                   10                  15

Pro Asp Leu Lys Ser Trp Leu Pro Ala Asp Asp Met Ala His Phe Ile
            20                  25                  30

Val Ala Ala Val Glu Arg Val Pro Met Ser Ala Phe Cys Val Pro Val
        35                  40                  45

Arg Thr Gly Gly Lys Ala Gln Tyr His Pro Arg Leu Met Leu Ala Leu
    50                  55                  60

Leu Ile Phe Ser Tyr Ala Asn Gly Leu Phe Ser Ser Arg Arg Ile Glu
65                  70                  75                  80

Arg Ala Thr Tyr Arg Asp Ile Gly Val Arg Phe Val Ala Ala Asn Leu
                85                  90                  95

His Pro Asp His Asp Thr Ile Ala Thr Phe Arg Arg Thr Asn Arg Gly
            100                 105                 110

Ala Ile Glu Ala Ala Phe Ala Gln Val Leu Leu Leu Ala Arg Glu Thr
        115                 120                 125

Gly Leu Leu Arg Leu Gly Val Val Ser Ile Asp Gly Thr Lys Ile Asp
    130                 135                 140

Ala Asp Ala Ser Lys Tyr Arg Ser Val Arg Tyr Asp Arg Ile Arg Ala
145                 150                 155                 160

Leu Arg Glu Gln Leu Ala Val Asp Ile Ala Lys Leu Met Asp Gln Ala
                165                 170                 175

Glu His Ala Asp Ala Thr Asp Ser Asp Pro Gln Ala Leu Pro Glu Glu
            180                 185                 190

Leu Ala Arg Arg Glu Ala Leu Lys Ala Lys Leu Asp Glu Ala Cys Ala
        195                 200                 205

Arg Leu Glu Ala Asp Ala Lys Ala Gln Ala Glu Ala Ala Arg Pro Ala
    210                 215                 220

Tyr Glu Lys Lys Lys Ala Val Tyr Asp Ala Lys Thr Gly Arg Arg Gly
225                 230                 235                 240

Arg Ala Pro Lys Pro Pro Asp Asp Glu Pro Pro Pro Asp Arg Gln Ile
                245                 250                 255

Ser Leu Thr Asp Pro Asp Ser Arg Leu Met Arg Arg Ser Asp Ala His
            260                 265                 270

Glu Phe Arg Gln Ala Tyr Asn Ala Gln Ala Val Val Cys Ala Glu Gly
        275                 280                 285

Ser Gln Leu Ile Val Thr Thr Gly Val Val Ala Thr Ser Ala Asp Ala
    290                 295                 300

Pro Ser Phe Ala Asp Thr Val Leu Ser Met Glu His Thr Ile Gly Leu
305                 310                 315                 320
```

```
Pro Glu Lys Val Leu Ala Asp Thr Gly Tyr Ala Ser Gly Gln Ala Val
                325                 330                 335

Arg Lys Leu Gln Glu Lys Gly Ile Asp Pro Leu Val Ala Ile Gly Arg
            340                 345                 350

Pro Cys Ala Arg Arg Pro Tyr Asp Phe Arg Pro His Pro Glu Ala Lys
        355                 360                 365

Glu Pro Arg Arg Ile Thr Glu Pro Trp Arg Leu Ala Met Lys Lys Lys
    370                 375                 380

Leu Glu Thr Thr Lys Ala Gly Asn Ile Tyr Arg Leu Arg Lys Gln Thr
385                 390                 395                 400

Val Glu Pro Val Phe Gly Ile Ile Lys Ser Ile Met Gly Phe Arg Arg
                405                 410                 415

Phe Ser Leu Arg Gly Leu Pro Lys Val Thr Thr Glu Trp Thr Leu Val
            420                 425                 430

Ala Leu Ala Tyr Asn Cys Lys Arg Met Ala Arg Leu His Ala Ala
        435                 440                 445


<210> SEQ ID NO 4
<211> LENGTH: 754
<212> TYPE: PRT
<213> ORGANISM: Komagataeibacter xylinus

<400> SEQUENCE: 4

Met Ser Glu Val Gln Ser Pro Val Pro Ala Glu Ser Arg Leu Asp Arg
1               5                   10                  15

Phe Ser Asn Lys Ile Leu Ser Leu Arg Gly Ala Asn Tyr Ile Val Gly
            20                  25                  30

Ala Leu Gly Leu Cys Ala Leu Ile Ala Ala Thr Thr Val Thr Leu Ser
        35                  40                  45

Ile Asn Glu Gln Leu Ile Val Ala Leu Val Cys Val Leu Val Phe Phe
    50                  55                  60

Ile Val Gly Arg Gly Lys Ser Arg Arg Thr Gln Ile Phe Leu Glu Val
65                  70                  75                  80

Leu Ser Ala Leu Val Ser Leu Arg Tyr Leu Thr Trp Arg Leu Thr Glu
                85                  90                  95

Thr Leu Asp Phe Asp Thr Trp Ile Gln Gly Gly Leu Gly Val Thr Leu
            100                 105                 110

Leu Ile Ala Glu Leu Tyr Ala Leu Tyr Met Leu Phe Leu Ser Tyr Phe
        115                 120                 125

Gln Thr Ile Gln Pro Leu His Arg Thr Pro Leu Pro Leu Pro Asp Asn
    130                 135                 140

Val Asp Asp Trp Pro Thr Val Asp Ile Phe Ile Pro Thr Tyr Asp Glu
145                 150                 155                 160

Gln Leu Ser Ile Val Arg Leu Thr Val Leu Gly Ala Leu Gly Ile Asp
                165                 170                 175

Trp Pro Pro Asp Lys Val Asn Val Tyr Ile Leu Asp Asp Gly Val Arg
            180                 185                 190

Pro Glu Phe Glu Gln Phe Ala Arg Glu Cys Gly Ser Leu Tyr Ile Gly
        195                 200                 205

Arg Val Asp Ser Ser His Ala Lys Ala Gly Asn Leu Asn His Ala Ile
    210                 215                 220

Lys Gln Thr Ser Gly Asp Tyr Ile Leu Ile Leu Asp Cys Asp His Ile
225                 230                 235                 240

Pro Thr Arg Ala Phe Leu Gln Ile Ala Met Gly Trp Met Val Ala Asp
```

-continued

```
            245                 250                 255

Arg Lys Ile Ala Leu Met Gln Thr Pro His His Phe Tyr Ser Pro Asp
        260                 265                 270

Pro Phe Gln Arg Asn Leu Ala Val Gly Tyr Arg Thr Pro Pro Glu Gly
    275                 280                 285

Asn Leu Phe Tyr Gly Val Ile Gln Asp Gly Asn Asp Phe Trp Asp Ala
    290                 295                 300

Thr Phe Phe Cys Gly Ser Cys Ala Ile Leu Arg Arg Glu Ala Ile Glu
305                 310                 315                 320

Ser Ile Gly Gly Phe Ala Val Glu Thr Val Thr Glu Asp Ala His Thr
            325                 330                 335

Ala Leu Arg Met Gln Arg Arg Gly Trp Ser Thr Ala Tyr Leu Arg Ile
        340                 345                 350

Pro Val Ala Ser Gly Leu Ala Thr Glu Arg Leu Thr Thr His Ile Gly
    355                 360                 365

Gln Arg Met Arg Trp Ala Arg Gly Met Ile Gln Ile Phe Arg Val Asp
    370                 375                 380

Asn Pro Met Leu Gly Ser Gly Leu Lys Leu Gly Gln Arg Leu Cys Tyr
385                 390                 395                 400

Leu Ser Ala Met Thr Ser Phe Phe Phe Ala Ile Pro Arg Val Ile Phe
            405                 410                 415

Leu Ala Ser Pro Leu Ala Phe Leu Phe Ala Gly Gln Asn Ile Ile Ala
        420                 425                 430

Ala Ser Pro Leu Ala Val Leu Ala Tyr Ala Ile Pro His Met Phe His
    435                 440                 445

Ser Ile Ala Thr Ala Ala Lys Val Asn Lys Gly Trp Arg Tyr Ser Phe
    450                 455                 460

Trp Ser Glu Val Tyr Glu Thr Thr Met Ala Leu Phe Leu Val Arg Val
465                 470                 475                 480

Thr Ile Ile Thr Met Met Phe Pro Ser Lys Gly Lys Phe Asn Val Thr
            485                 490                 495

Glu Lys Gly Gly Val Leu Glu Glu Glu Glu Phe Asp Leu Gly Ala Thr
        500                 505                 510

Tyr Pro Asn Ile Ile Phe Ala Val Ile Met Ala Leu Gly Leu Leu Ile
    515                 520                 525

Gly Leu Phe Glu Leu Ile Phe His Phe Ser Gln Leu Asp Gly Ile Ala
    530                 535                 540

Met Arg Ala Tyr Ala Leu Asn Cys Ile Trp Ala Ala Ile Ser Leu Ile
545                 550                 555                 560

Ile Leu Leu Ala Ala Ile Ala Val Gly Arg Glu Thr Lys Gln Val Arg
            565                 570                 575

Tyr Ser His Arg Ile Asp Ala His Ile Pro Val Thr Val Tyr Glu Ala
        580                 585                 590

Pro Val Ala Gly Gln Pro Asn Thr Tyr His Asn Ala Thr Pro Gly Met
    595                 600                 605

Thr Gln Asp Val Ser Met Gly Gly Val Ala Val His Met Pro Trp Pro
    610                 615                 620

Asp Ile Gly Ser Gly Pro Val Lys Thr Arg Ile His Ala Val Leu Asp
625                 630                 635                 640

Gly Glu Glu Ile Asp Ile Pro Ala Thr Met Leu Arg Cys Lys Asn Gly
            645                 650                 655

Lys Ala Val Phe Thr Trp Asp Asn Asn Asp Leu Asp Thr Glu Arg Asp
        660                 665                 670
```

-continued

```
Ile Val Arg Phe Val Phe Gly Arg Ala Asp Ala Trp Leu Gln Trp Asn
        675                 680                 685

Asn Tyr Glu Asp Asp Arg Pro Leu Arg Ser Leu Trp Ser Leu Leu Leu
    690                 695                 700

Ser Ile Lys Ala Leu Phe Arg Lys Lys Gly Lys Met Met Ala Asn Ser
705                 710                 715                 720

Arg Pro Thr Lys Lys Pro Arg Ala Leu Pro Val Glu Arg Arg Glu Pro
                725                 730                 735

Thr Thr Ile Gln Ser Gly Gln Thr Gln Glu Gly Lys Ile Ser Arg Ala
            740                 745                 750

Ala Ser


<210> SEQ ID NO 5
<211> LENGTH: 2265
<212> TYPE: DNA
<213> ORGANISM: Artificial Sequence
<220> FEATURE:
<223> OTHER INFORMATION: Synthetic BcsA gene having modified insertion
      recognition sequence

<400> SEQUENCE: 5

atgtcagagg ttcagtcgcc agtacccgcg gagagtagat tggaccgctt ttccaacaag     60

atactgtcac tgcgtggggc caactatata gttggagcgc tggggctttg tgcacttatc    120

gccgcaacca cggttacgct gtccattaat gagcagctga ttgtggcact tgtgtgtgtg    180

ctcgtctttt tcattgtcgg gcggggcaag agccggcgta cccagatctt tctcgaggtg    240

ctctcggcgc tggtttccct gcgttacctg acatggcgcc tgaccgaaac gctggacttc    300

gacacatgga ttcagggcgg gctgggtgtg accctgctca tcgccgagct gtatgccctg    360

tacatgctgt ttctcagcta tttccagaca atccagccgc ttcatcgcac gccgctcccc    420

ctgccggaca atgttgatga ctggcccacc gtcgatatct tcatcccgac ctatgatgaa    480

cagctgagca tcgtgcgcct gaccgtgctg ggcgcgctgg gtatcgactg gccacccgat    540

aaagtgaatg tctatatcct tgatgatggc gtgcgcccgg aattcgaaca gtttgccagg    600

gaatgtggtt ccctttacat cgggcgcgtg gacagttcgc acgccaaggc gggtaaccta    660

aaccacgcca ttaagcagac aagcggcgat tacatcctca tcctggattg tgaccatatt    720

ccgacacgcg cgttcctgca gatcgcgatg ggctggatgg tcgccgaccg caagattgcc    780

ctgatgcaga cgccgcatca cttctactcc cccgatccgt tccagcgtaa cctcgccgtg    840

ggatatcgca ccccgccgga aggcaacctg ttctacggcg tcattcagga tggtaacgac    900

ttctgggatg ccaccttctt ctgcggctcg tgcgccatcc tgcgccgtga ggcgattgaa    960

tcgatcggcg gcttcgcggt tgaaaccgtg acggaagatg cccataccgc cctgcgcatg   1020

cagcgccgtg gctggtccac tgcctacttg cgcattcctg tggccagtgg cctggctacc   1080

gagcgcctga caacccatat cggccagcgc atgcgctggg cgcgcggcat gatccagatc   1140

ttccgcgtgg ataatccgat gcttgggtcg gggctgaagc ttggccagcg gctgtgctac   1200

ctctcggcta tgacgtcgtt cttcttcgcc attccgcgcg tcatcttcct cgcctcgccg   1260

ctggcgttcc tgttcgcggg ccagaacatc atcgccgcct cgccgctggc cgttctggcc   1320

tacgccattc cgcatatgtt ccactccatc gcgaccgccg ccaaggtaaa caagggctgg   1380

cgctactcgt tctggagtga agtgtacgaa accaccatgg cgctgttcct ggtgcgcgtg   1440

accatcatca ccatgatgtt cccctctaag ggcaagttca acgtgacgga aaagggtggg   1500
```

-continued

```
gtgctggagg aggaagagtt cgatcttggc gcgacctacc ccaacatcat ctttgccgtc   1560

atcatggcgc ttggcctgct gatcggcctg ttcgaactga tcttccactt cagccagctt   1620

gatggcatcg ccatgcgcgc ctacgcgctg aactgcatct gggccgcgat cagtctcatc   1680

atccttctgg ctgccattgc ggtggggcgt gaaaccaaac aggtccgtta cagccatcgt   1740

atcgatgcgc atatcccggt aacggtttat gaagcgccgg tcgcggggca gcccaatacc   1800

taccataatg cgacaccggg catgacccag gatgtttcca tgggtggtgt tgccgtgcat   1860

atgccctggc ccgatatcgg ctcggggccg gtcaagacac gtatccatgc cgtgctcgat   1920

ggcgaggaga tcgatattcc cgccaccatg ctgcgctgca agaatggcaa ggccgtgttc   1980

acatgggaca ataatgacct tgatacggaa cgcgatatcg tccgcttcgt gttcgggcgg   2040

gccgatgcct ggctgcaatg gaataattat gaggatgaca ggccgctacg cagcctgtgg   2100

agcctgctgc tcagcattaa ggcgctgttc cgcaaaaaag gcaaaatgat ggccaatagt   2160

cgtccaacaa aaaaaccacg tgcactaccg gttgagcgca gggagcccac aaccatccag   2220

agtggacaga cacaggaagg aaagatcagc cgtgcggcct cgtga                   2265
```

<210> SEQ ID NO 6
<211> LENGTH: 776
<212> TYPE: DNA
<213> ORGANISM: Artificial Sequence
<220> FEATURE:
<223> OTHER INFORMATION: Synthetic upper arm_pUC19(776 bp)

<400> SEQUENCE: 6

```
taacgactcc ggcatatgag cccgcgccgc agccagctcc ggcccctgtt gtgcaggccg     60

cgccgtcgca gtcggcagca gccgtgacgc catcggcccc tgaagtgccg ccccagcccg    120

taaggcagga gcggccggta gtgccgccag tgccgcccag gcctgcggtg tcttccttca    180

tggcgccgcg tcctgcggct ccggcttttg gcacgacagc gtcagccacg ccccctgttg    240

cggtggagga ctgggcgccc gtgcccaagg cccagcagca gcgtgggcag cgtttgacag    300

gaccaggctt ctttttcggc gccggaagcg aacgggcgcc cgcagcaagg ctgttccagt    360

cagcaccggt gtcccggcct gtttcaaaac ctgtttccaa ggtgaccaca atgaccaaag    420

ttgacaagat ttccccgaat gacagtcagg ctgggcgtcc cgtgccgacc gacaattccc    480

cgaccctgac cgaagtgttc atgacccttg gcggtcgggc cacggaccgg ttggtgccca    540

agcccagcct gcgcgatgcc ctgttgcgca agcgtgaaga cgcgaacggc gactcctgaa    600

accgtgccgg gggtgacctg ctcccggcat gccagaggaa ggaaggggaa aggttttccc    660

cgccccgcat ccgctgcggg ccgaaaggcg acatgacgga ccgaatgcgt ctgacggttt    720

tcttttgaat atataacgac ctgttttacc agtatttatt atcggacgag ctattg        776
```

<210> SEQ ID NO 7
<211> LENGTH: 908
<212> TYPE: DNA
<213> ORGANISM: Artificial Sequence
<220> FEATURE:
<223> OTHER INFORMATION: Synthetic lower arm_pUC19(908 bp)

<400> SEQUENCE: 7

```
atgtcagagg ttcagtcgcc agtacccgcg gagagtaggc tagaccgctt ttccaacaag     60

atactgtcac tgcgtggggc caactatata gttggagcgc tggggctttg tgcacttatc    120

gccgcaacca cggttacgct gtccattaat gagcagctga ttgtggcact tgtgtgtgtg    180

ctcgtctttt tcattgtcgg gcggggcaag agccggcgta cccagatctt tctcgaggtg    240
```

-continued

```
ctctcggcgc tggtttccct gcgttacctg acatggcgcc tgaccgaaac gctggacttc    300

gacacatgga ttcagggcgg gctgggtgtg accctgctca tcgccgagct gtatgccctg    360

tacatgctgt ttctcagcta tttccagaca atccagccgc ttcatcgcac gccgctcccc    420

ctgccggaca atgttgatga ctggcccacc gtcgatatct tcatcccgac ctatgatgaa    480

cagctgagca tcgtgcgcct gaccgtgctg ggcgcgctgg gtatcgactg gccacccgat    540

aaagtgaatg tctatatcct tgatgatggc gtgcgcccgg aattcgaaca gtttgccagg    600

gaatgtggtt ccctttacat cgggcgcgtg gacagttcgc acgccaaggc gggtaaccta    660

aaccacgcca ttaagcagac aagcggcgat tacatcctca tcctggattg tgaccatatt    720

ccgacacgcg cgttcctgca gatcgcgatg ggctggatgg tcgccgaccg caagattgcc    780

ctgatgcaga cgccgcatca cttctactcc cccgatccgt tccagcgtaa cctcgccgtg    840

ggatatcgca ccccgccgga aggcaacctg ttctacggcg tcattcagga tggtaacgac    900

ttctggga                                                             908
```

<210> SEQ ID NO 8
<211> LENGTH: 34
<212> TYPE: DNA
<213> ORGANISM: Artificial Sequence
<220> FEATURE:
<223> OTHER INFORMATION: Synthetic upper arm_F

<400> SEQUENCE: 8

```
gacggccagt gaatttaacg actccggcat atga                                 34
```

<210> SEQ ID NO 9
<211> LENGTH: 41
<212> TYPE: DNA
<213> ORGANISM: Artificial Sequence
<220> FEATURE:
<223> OTHER INFORMATION: Synthetic upper arm_R

<400> SEQUENCE: 9

```
gatttacgac ctgcacagcc caatagctcg tccgataata a                         41
```

<210> SEQ ID NO 10
<211> LENGTH: 21
<212> TYPE: DNA
<213> ORGANISM: Artificial Sequence
<220> FEATURE:
<223> OTHER INFORMATION: Synthetic lower arm_F

<400> SEQUENCE: 10

```
tcggacgagc tattgatgtc a                                               21
```

<210> SEQ ID NO 11
<211> LENGTH: 35
<212> TYPE: DNA
<213> ORGANISM: Artificial Sequence
<220> FEATURE:
<223> OTHER INFORMATION: Synthetic lower arm_R

<400> SEQUENCE: 11

```
tgattacgcc agctttccca gaagtcgtta ccatc                                35
```

<210> SEQ ID NO 12
<211> LENGTH: 4843
<212> TYPE: DNA
<213> ORGANISM: Artificial Sequence
<220> FEATURE:

-continued

<223> OTHER INFORMATION: Synthetic pTsaP plasmid

<400> SEQUENCE: 12

```
aagaacatgt gagcaaaagg ccagcaaaag gccaggaacc gtaaaaaggc cgcgttgctg     60
gcgtttttcc ataggctccg cccccctgac gagcatcaca aaaatcgacg ctcaagtcag    120
aggtggcgaa acccgacagg actataaaga taccaggcgt ttccccctgg aagctccctc    180
gtgcgctctc ctgttccgac cctgccgctt accggatacc tgtccgcctt tctcccttcg    240
ggaagcgtgg cgctttctca tagctcacgc tgtaggtatc tcagttcggt gtaggtcgtt    300
cgctccaagc tgggctgtgt gcacgaaccc cccgttcagc ccgaccgctg cgccttatcc    360
ggtaactatc gtcttgagtc caacccggta agacacgact tatcgccact ggcagcagcc    420
actggtaaca ggattagcag agcgaggtat gtaggcggtg ctacagagtt cttgaagtgg    480
tggcctaact acggctacac tagaagaaca gcatttggta tctgcgctct gctgaagcca    540
gttaccttcg gaaaaagagt tggtagctct tgatccggca aacaaaccac cgctggtagc    600
ggtggttttt ttgtttgcaa gcagcagatt acgcgcagaa aaaaaggatc tcaagaagat    660
cctttgatct tttctacggg gtctgacgct cagtggaacg aaaactcacg ttaattctca    720
tgtttgacag cttatcatcg ataagcttta atgcggtagt ttatcacagt taaattgcta    780
acgcagtcag gcaccgtgta tgaaatctaa caatgcgctc atcgtcatcc tcggcaccgt    840
caccctggat gctgtaggca taggcttggt tatgccggta ctgccgggcc tcttgcggga    900
tatcgtccat tccgacagca tcgccagtca ctatggcgtg ctgctagcgc tatatgcgtt    960
gatgcaattt ctatgcgcac ccgttctcgg agcactgtcc gaccgctttg gccgccgccc   1020
agtcctgctc gcttcgctac ttggagccac tatcgactac gcgatcatgg cgaccacacc   1080
cgtcctgtgg atcctctacg ccggacgcat cgtggccggc atcaccggcg ccacaggtgc   1140
ggttgctggc gcctatatcg ccgacatcac cgatggggaa gatcgggctc gccacttcgg   1200
gctcatgagc gcttgtttcg gcgtgggtat ggtggcaggc cccgtggccg ggggactgtt   1260
gggcgccatc tccttgcatg caccattcct tgcggcggcg gtgctcaacg gcctcaacct   1320
actactgggc tgcttcctaa tgcaggagtc gcataaggga gagcgtcgac cgatgccctt   1380
gagagccttc aacccagtca gctccttccg gtgggcgcgg ggcatgacta tcgtcgccgc   1440
acttatgact gtcttcttta tcatgcaact cgtaggacag gtgccggcag cgctctgggt   1500
cattttcggc gaggaccgct ttcgctggag cgcgacgatg atcggcctgt cgcttgcggt   1560
attcggaatc ttgcacgccc tcgctcaagc cttcgtcact ggtcccgcca ccaaacgttt   1620
cggcgagaag caggccatta tcgccggcat ggcggccgac gcgctgggct acgtcttgct   1680
ggcgttcgcg acgcgaggct ggatggcctt ccccattatg attcttctcg cttccggcgg   1740
catcgggatg cccgcgttgc aggccatgct gtccaggcag gtagatgacg accatcaggg   1800
acagcttcaa ggatcgctcg cggctcttac cagcctaact tcgatcactg gaccgctgat   1860
cgtcacggcg atttatgccg cctcggcgag cacatggaac gggttggcat ggattgtagg   1920
cgccgcccta taccttgtct gcctccccgc gttgcgtcgc ggtgcatgga gccgggccac   1980
ctcgacctga atggaagccg gcggcacctc gctaacggat tcaccactcc aagaattgga   2040
gccaattttt aaggcagtta ttggtgccct taaacgcctg gttgctacgc ctgaataagt   2100
gataataagc ggatgaatgg cagaaattcg aattcagcca gcaagacagc gatagagggt   2160
agttatccac gtgaaaccgc taatgccccg caaagccttg attcacgggg ctttccggcc   2220
cgctccaaaa actatccacg tgaaatcgct aatcagggta cgtgaaatcg ctaatcggag   2280
```

-continued

```
tacgtgaaat cgctaataag gtcacgtgaa atcgctaatc aaaaaggcac gtgagaacgc   2340
taatagccct ttcagatcaa cagcttgcaa acacccctcg ctccggcaag tagttacagc   2400
aagtagtatg ttcaattagc ttttcaatta tgaatatata tatcaattat tggtcgccct   2460
tggcttgtgg acaatgcgct acgcgcaccg gctccgcccg tggacaaccg caagcggttg   2520
cccaccgtcg agcgccagcg cctttgccca caacccggcg gccggccgca acagatcgtt   2580
ttataaattt tttttttga aaaagaaaaa gcccgaaagg cggcaacctc tcgggcttct   2640
ggatttccga tcacctgtaa agtgggacca catgctgaac tccctatcac tgcatgagta   2700
gggaactgcc aggcatcaaa taaaacgaaa ggctcagtcg aaagactggg cctttcgttt   2760
tatctgttgt ttgtcggtga acgctctcct gagtaggaca aatccgccgg gagcggattt   2820
gaacgttgcg aagcaacggc ccggagggtg gcgggcagga cgcccgccat aaactgccag   2880
gcatcaaatt aagcagaagg ccatcctgac ggatggcctt tttgcgtttc tacaaactct   2940
gcaggtcgac tctagagatc taacttcggc ggcgcccgag cgtgaacagc acgggctgac   3000
caacctgtgc gcgcgcggcg gctacgtcct ggcggaagcc gaagggacgc ggcaggtcac   3060
gctggtcgcc acggggcacg aggcgatact ggcgctggcg gcacgcaaac tgttgaagga   3120
cgcaggggtt gcggcggctg tcgtatccct tccatgctgg gaactgttcg ccgcgcaaaa   3180
aatgacgtat cgtgccgccg tgctgggaac ggcaccccgg atcggcattg aagccgcgtc   3240
agggtttgga tgggaacgct ggcttgggac agacgggctg tttgttggca ttgacgggtt   3300
cgggacggcc gccccggacc agccggacag cgcgactgac atcacgccgg aacggatctg   3360
ccgcgacgcg ctgcgtctgg tccgtcccct gtccgatacc ctgactgaac cggcgggagg   3420
aaacggcgcg ccgcccggga tgacatcggc cgatgtcagt gtgtgaagat ctcccgggta   3480
ccgagctctc tagaaagaag gagggacgag ctattgatgg agaaaaaaat cactggatat   3540
accaccgttg atatatccca atggcatcgt aaagaacatt ttgaggcatt tcagtcagtt   3600
gctcaatgta cctataacca gaccgttcag ctggatatta cggccttttt aaagaccgta   3660
aagaaaaata agcacaagtt ttatccggcc tttattcaca ttcttgcccg cctgatgaat   3720
gctcatccgg aattccgtat ggcaatgaaa gacggtgagc tggtgatatg ggatagtgtt   3780
cacccttgtt acaccgtttt ccatgagcaa actgaaacgt tttcatcgct ctggagtgaa   3840
taccacgacg atttccggca gtttctacac atatattcgc aagatgtggc gtgttacggt   3900
gaaaacctgg cctatttccc taaagggttt attgagaata tgtttttcgt ctcagccaat   3960
ccctgggtga gtttcaccag ttttgattta aacgtggcca atatggacaa cttcttcgcc   4020
cccgttttca ccatgggcaa atattatacg caaggcgaca aggtgctgat gccgctggcg   4080
attcaggttc atcatgccgt ttgtgatggc ttccatgtcg gcagaatgct taatgaatta   4140
caacagtact gcgatgagtg gcagggcggg gcgtaatttt tttaaggcag ttattggtgc   4200
ccttaaacgc ctggttgcta cgcctgaata agtgataata agcggatgaa tggcagaaat   4260
tcgtcgaggc ggcacctcgc taacggattc accactccaa gaattggagc caatcaattc   4320
ttgcggagaa ctgtgaatgc gcaaaccaac ccttggcaga acatatccat cgcgtccgcc   4380
atctccagca gccgcacgcg gcgcatctcg gctgttttgg cggatgagag aagattttca   4440
gcctgataca gattaaatca gaacgcagaa gcggtctgat aaaacagaat ttgcctggcg   4500
gcagtagcgc ggtggtccca cctgacccca tgccgaactc agaagtgaaa cgccgtagcg   4560
ccgatggtag tgtggggtct ccccatgcga gagtagggaa ctgccaggca tcaaataaaa   4620
```

-continued cgaaaggctc agtcgaaaga ctgggccttt cgttttatct gttgtttgtc ggtgaacgct 4680
ctcctgagta ggacaaatcc gccgggagcg gatttgaacg ttgcgaagca acggcccgga 4740
gggtggcggg caggacgccc gccataaact gccaggcatc aaattaagca gaaggccatc 4800
ctgacggatg gcctttttgc gtttctacaa actcttcctg tcg 4843

<210> SEQ ID NO 13
<211> LENGTH: 21
<212> TYPE: DNA
<213> ORGANISM: Artificial Sequence
<220> FEATURE:
<223> OTHER INFORMATION: Synthetic Ptac_F

<400> SEQUENCE: 13
ggctgtgcag gtcgtaaatc a 21

<210> SEQ ID NO 14
<211> LENGTH: 36
<212> TYPE: DNA
<213> ORGANISM: Artificial Sequence
<220> FEATURE:
<223> OTHER INFORMATION: Synthetic Ptac_R

<400> SEQUENCE: 14
tccagtgatt tttttctcca tcaatagctc gtccct 36

<210> SEQ ID NO 15
<211> LENGTH: 21
<212> TYPE: DNA
<213> ORGANISM: Artificial Sequence
<220> FEATURE:
<223> OTHER INFORMATION: Synthetic Cat_F

<400> SEQUENCE: 15
atggagaaaa aaatcactgg a 21

<210> SEQ ID NO 16
<211> LENGTH: 41
<212> TYPE: DNA
<213> ORGANISM: Artificial Sequence
<220> FEATURE:
<223> OTHER INFORMATION: Synthetic Cat_R

<400> SEQUENCE: 16
gctcgggcgc cgccgaagtt ttacgccccg ccctgccact c 41

<210> SEQ ID NO 17
<211> LENGTH: 3810
<212> TYPE: DNA
<213> ORGANISM: Artificial Sequence
<220> FEATURE:
<223> OTHER INFORMATION: Synthetic pTsa_EX2 plasmid

<400> SEQUENCE: 17
gaattcagcc agcaagacag cgatagaggg tagttatcca cgtgaaaccg ctaatgcccc 60
gcaaagcctt gattcacggg gctttccggc ccgctccaaa aactatccac gtgaaatcgc 120
taatcagggt acgtgaaatc gctaatcgga gtacgtgaaa tcgctaataa ggtcacgtga 180
aatcgctaat caaaaaggca cgtgagaacg ctaatagccc tttcagatca acagcttgca 240
aacacccctc gctccggcaa gtagttacag caagtagtat gttcaattag cttttcaatt 300
atgaatatat atatcaatta ttggtcgccc ttggcttgtg gacaatgcgc tacgcgcacc 360
ggctccgccc gtggacaacc gcaagcggtt gcccaccgtc gagcgccagc gcctttgccc 420

-continued

```
acaacccggc ggccggccgc aacagatcgt tttataaatt tttttttttg aaaaagaaaa    480
agcccgaaag gcggcaacct ctcgggcttc tggatttccg atcacctgta agtcggacga    540
acttcggcgg cgcccgagcg tgaacagcac gggctgacca acctgtgcgc gcggggcggt    600
tacgtgctgg ccgaagccga aggcgcgcga caggtcacgc tgatcgccac gggacatgag    660
gccatactgg cactggcggc gcgcaaactg ctgcgggacg cgggggttgc ggcggctgtc    720
gtctcccttc catgctggga actgttcgcc gtgcaaaaaa tgacgtatcg tgccgccgtg    780
ctgggaacgg caccccggat cggggatcgag gccgcttcag ggtttggatg ggaacgatgg    840
cttggaacag gcgggctgtt tgtcggtatt gacggattcg ggcgtctta cgcccccgac    900
cggccagaca gccctgccgg catcacgccg gaacggatct gccacgacgc attgcggctg    960
gtccgccccc atgccgacgc cctggttgaa accgcgggag gaaacggcgc gccgcccggg   1020
atggcatcgg tcgatgccag tgtgtgaaat gtcagacctt acggagaaaa taagaaaagg   1080
acgagctatt gattcgtacc cggggatcct ctagagtcga cctgcaggca tgcaagcttg   1140
gctgttttgg cggatgagag aagattttca gcctgataca gattaaatca gaacgcagaa   1200
gcggtctgat aaaacagaat ttgcctggcg gcagtagcgc ggtggtccca cctgacccca   1260
tgccgaactc agaagtgaaa cgccgtagcg ccgatggtag tgtggggtct ccccatgcga   1320
gagtagggaa ctgccaggca tcaaataaaa cgaaaggctc agtcgaaaga ctgggccttt   1380
cgttttatct gttgtttgtc ggtgaacgct ctcctgagta ggacaaatcc gccgggagcg   1440
gatttgaacg ttgcgaagca acggcccgga gggtggcggg caggacgccc gccataaact   1500
gccaggcatc aaattaagca gaaggccatc ctgacggatg gcctttttgc aagaacatgt   1560
gagcacttcc gcttcctcgc tcactgactc gctgcgctcg gtcgttcggc tgcggcgagc   1620
ggtatcagct cactcaaagg cggtaatacg gttatccaca gaatcagggg ataacgcagg   1680
aaagaacatg tgagcaaaag gccagcaaaa ggccaggaac cgtaaaaagg ccgcgttgct   1740
ggcgtttttc cataggctcc gcccccctga cgagcatcac aaaaatcgac gctcaagtca   1800
gaggtggcga aacccgacag gactataaag ataccaggcg tttccccctg gaagctccct   1860
cgtgcgctct cctgttccga ccctgccgct taccggatac ctgtccgcct ttctcccttc   1920
gggaagcgtg gcgctttctc atagctcacg ctgtaggtat ctcagttcgg tgtaggtcgt   1980
tcgctccaag ctgggctgtg tgcacgaacc ccccgttcag cccgaccgct gcgccttatc   2040
cggtaactat cgtcttgagt ccaacccggt aagacacgac ttatcgccac tggcagcagc   2100
cactggtaac aggattagca gagcgaggta tgtaggcggt gctacagagt tcttgaagtg   2160
gtggcctaac tacggctaca ctagaagaac agcatttggt atctgcgctc tgctgaagcc   2220
agttaccttc ggaaaaagag ttggtagctc ttgatccggc aaacaaacca ccgctggtag   2280
cggtggtttt tttgtttgca agcagcagat tacgcgcaga aaaaaaggat ctcaagaaga   2340
tcctttgatc ttttctacgg ggtctgacgc tcagtggaac gaaaactcac gttaattctc   2400
atgtttgaca gcttatcatc gataagcttt aatgcggtag tttatcacag ttaaattgct   2460
aacgcagtca ggcaccgtgt atgaaatcta acaatgcgct catcgtcatc ctcggcaccg   2520
tcaccctgga tgctgtaggc ataggcttgg ttatgccggt actgccgggc ctcttgcggg   2580
atatcgtcca ttccgacagc atcgccagtc actatggcgt gctgctagcg ctatatgcgt   2640
tgatgcaatt tctatgcgca cccgttctcg gagcactgtc cgaccgcttt ggccgccgcc   2700
cagtcctgct cgcttcgcta cttggagcca ctatcgacta cgcgatcatg gcgaccacac   2760
```

ccgtcctgtg gatcctctac gccggacgca tcgtggccgg catcaccggc gccacaggtg 2820
cggttgctgg cgcctatatc gccgacatca ccgatgggga agatcgggct cgccacttcg 2880
ggctcatgag cgcttgtttc ggcgtgggta tggtggcagg ccccgtggcc gggggactgt 2940
tgggcgccat ctccttgcat gcaccattcc ttgcggcggc ggtgctcaac ggcctcaacc 3000
tactactggg ctgcttccta atgcaggagt cgcataaggg agagcgtcga ccgatgccct 3060
tgagagcctt caacccagtc agctccttcc ggtgggcgcg gggcatgact atcgtcgccg 3120
cacttatgac tgtcttcttt atcatgcaac tcgtaggaca ggtgccggca gcgctctggg 3180
tcattttcgg cgaggaccgc tttcgctgga gcgcgacgat gatcggcctg tcgcttgcgg 3240
tattcggaat cttgcacgcc ctcgctcaag ccttcgtcac tggtcccgcc accaaacgtt 3300
tcggcgagaa gcaggccatt atcgccggca tggcggccga cgcgctgggc tacgtcttgc 3360
tggcgttcgc gacgcgaggc tggatggcct tccccattat gattcttctc gcttccggcg 3420
gcatcgggat gcccgcgttg caggccatgc tgtccaggca ggtagatgac gaccatcagg 3480
gacagcttca aggatcgctc gcggctctta ccagcctaac ttcgatcact ggaccgctga 3540
tcgtcacggc gatttatgcc gcctcggcga gcacatggaa cgggttggca tggattgtag 3600
gcgccgccct ataccttgtc tgcctccccg cgttgcgtcg cggtgcatgg agccgggcca 3660
cctcgacctg aatggaagcc ggcggcacct cgctaacgga ttcaccactc caagaattgg 3720
agccaatttt taaggcagtt attggtgccc ttaaacgcct ggttgctacg cctgaataag 3780
tgataataag cggatgaatg gcagaaattc 3810

<210> SEQ ID NO 18
<211> LENGTH: 21
<212> TYPE: DNA
<213> ORGANISM: Artificial Sequence
<220> FEATURE:
<223> OTHER INFORMATION: Synthetic PgapA_F

<400> SEQUENCE: 18
aacttcggcg gcgcccgagc g 21

<210> SEQ ID NO 19
<211> LENGTH: 41
<212> TYPE: DNA
<213> ORGANISM: Artificial Sequence
<220> FEATURE:
<223> OTHER INFORMATION: Synthetic PgapA_R

<400> SEQUENCE: 19
gacatcaata gctcgtccga tttcttattt tctccgtaag g 41

<210> SEQ ID NO 20
<211> LENGTH: 5773
<212> TYPE: DNA
<213> ORGANISM: Artificial Sequence
<220> FEATURE:
<223> OTHER INFORMATION: Synthetic pUC19_bcsA plasmid

<400> SEQUENCE: 20
gaattcactg gccgtcgttt tacaacgtcg tgactgggaa aaccctggcg ttacccaact 60
taatcgcctt gcagcacatc cccctttcgc cagctggcgt aatagcgaag aggcccgcac 120
cgatcgccct tcccaacagt tgcgcagcct gaatggcgaa tggcgcctga tgcggtattt 180
tctccttacg catctgtgcg gtatttcaca ccgcatatgg tgcactctca gtacaatctg 240
ctctgatgcc gcatagttaa gccagccccg acacccgcca acacccgctg acgcgccctg 300

-continued

```
acgggcttgt ctgctcccgg catccgctta cagacaagct gtgaccgtct ccgggagctg    360
catgtgtcag aggttttcac cgtcatcacc gaaacgcgcg agacgaaagg gcctcgtgat    420
acgcctattt ttataggtta atgtcatgat aataatggtt tcttagacgt caggtggcac    480
ttttcgggga aatgtgcgcg gaacccctat ttgtttattt ttctaaatac attcaaatat    540
gtatccgctc atgagacaat aaccctgata aatgcttcaa taatattgaa aaaggaagag    600
tatgagtatt caacatttcc gtgtcgccct tattcccttt tttgcggcat tttgccttcc    660
tgtttttgct cacccagaaa cgctggtgaa agtaaaagat gctgaagatc agttgggtgc    720
acgagtgggt tacatcgaac tggatctcaa cagcggtaag atccttgaga gttttcgccc    780
cgaagaacgt tttccaatga tgagcacttt taaagttctg ctatgtggcg cggtattatc    840
ccgtattgac gccgggcaag agcaactcgg tcgccgcata cactattctc agaatgactt    900
ggttgagtac tcaccagtca cagaaaagca tcttacggat ggcatgacag taagagaatt    960
atgcagtgct gccataacca tgagtgataa cactgcggcc aacttacttc tgacaacgat   1020
cggaggaccg aaggagctaa ccgctttttt gcacaacatg ggggatcatg taactcgcct   1080
tgatcgttgg gaaccggagc tgaatgaagc cataccaaac gacgagcgtg acaccacgat   1140
gcctgtagca atggcaacaa cgttgcgcaa actattaact ggcgaactac ttactctagc   1200
ttcccggcaa caattaatag actggatgga ggcggataaa gttgcaggac cacttctgcg   1260
ctcggccctt ccggctggct ggtttattgc tgataaatct ggagccggtg agcgtgggtc   1320
tcgcggtatc attgcagcac tggggccaga tggtaagccc tcccgtatcg tagttatcta   1380
cacgacgggg agtcaggcaa ctatggatga acgaaataga cagatcgctg agataggtgc   1440
ctcactgatt aagcattggt aactgtcaga ccaagtttac tcatatatac tttagattga   1500
tttaaaactt catttttaat ttaaaaggat ctaggtgaag atcctttttg ataatctcat   1560
gaccaaaatc ccttaacgtg agttttcgtt ccactgagcg tcagaccccg tagaaaagat   1620
caaaggatct tcttgagatc cttttttTct gcgcgtaatc tgctgcttgc aaacaaaaaa   1680
accaccgcta ccagcggtgg tttgtttgcc ggatcaagag ctaccaactc tttttccgaa   1740
ggtaactggc ttcagcagag cgcagatacc aaatactgtt cttctagtgt agccgtagtt   1800
aggccaccac ttcaagaact ctgtagcacc gcctacatac ctcgctctgc taatcctgtt   1860
accagtggct gctgccagtg gcgataagtc gtgtcttacc gggttggact caagacgata   1920
gttaccggat aaggcgcagc ggtcgggctg aacggggggt tcgtgcacac agcccagctt   1980
ggagcgaacg acctacaccg aactgagata cctacagcgt gagctatgag aaagcgccac   2040
gcttcccgaa gggagaaagg cggacaggta tccggtaagc ggcagggtcg gaacaggaga   2100
gcgcacgagg gagcttccag ggggaaacgc ctggtatctt tatagtcctg tcgggtttcg   2160
ccacctctga cttgagcgtc gatttttgtg atgctcgtca ggggggcgga gcctatggaa   2220
aaacgccagc aacgcggcct ttttacggtt cctggccttt tgctggcctt ttgctcacat   2280
gttctttcct gcgttatccc ctgattctgt ggataaccgt attaccgcct ttgagtgagc   2340
tgataccgct cgccgcagcc gaacgaccga gcgcagcgag tcagtgagcg aggaagcgga   2400
agagcgccca atacgcaaac cgcctctccc cgcgcgttgg ccgattcatt aatgcagctg   2460
gcacgacagg tttcccgact ggaaagcggg cagtgagcgc aacgcaatta atgtgagtta   2520
gctcactcat taggcacccc aggctttaca ctttatgctt ccggctcgta tgttgtgtgg   2580
aattgtgagc ggataacaat ttcacacagg aaacagctat gaccatgatt acgccaagct   2640
```

```
ttaacgactc cggcatatga gcccgcgccg cagccagctc cggcccctgt tgtgcaggcc   2700
gcgccgtcgc agtcggcagc agccgtgacg ccatcggccc ctgaagtgcc gccccagccc   2760
gtaaggcagg agcggccggt agtgccgcca gtgccgccca ggcctgcggt gtcttccttc   2820
atggcgccgc gtcctgcggc tccggctttt ggcacgacag cgtcagccac gcccccctgtt  2880
gcggtggagg actgggcgcc cgtgcccaag gcccagcagc agcgtgggca gcgtttgaca   2940
ggaccaggct tctttttcgg cgccggaagc gaacgggcgc ccgcagcaag gctgttccag   3000
tcagcaccgg tgtcccggcc tgtttcaaaa cctgtttcca aggtgaccac aatgaccaaa   3060
gttgacaaga tttccccgaa tgacagtcag gctgggcgtc ccgtgccgac cgacaattcc   3120
ccgaccctga ccgaagtgtt catgaccctt ggcggtcggg ccacggaccg gttggtgccc   3180
aagcccagcc tgcgcgatgc cctgttgcgc aagcgtgaag acgcgaacgg cgactcctga   3240
aaccgtgccg ggggtgacct gctcccggca tgccagagga aggaagggga aaggttttcc   3300
ccgccccgca tccgctgcgg gccgaaaggc gacatgacgg accgaatgcg tctgacggtt   3360
ttcttttgaa tatataacga cctgttttac cagtatttat tatcggacga gctattgggc   3420
tgtgcaggtc gtaaatcact gcataattcg tgtcgctcaa ggcgcactcc cgttctggat   3480
aatgtttttt gcgccgacat cataacggtt ctggcaaata ttctgaaatg agctgttgac   3540
aattaatcat cggctcgtat aatgtgtgga attgtgagcg gataacaatt tcacacagga   3600
aacatagatc tcccgggtac cgagctctct agaaagaagg agggacgagc tattgatgga   3660
gaaaaaaatc actggatata ccaccgttga tatatcccaa tggcatcgta aagaacattt   3720
tgaggcattt cagtcagttg ctcaatgtac ctataaccag accgttcagc tggatattac   3780
ggccttttta aagaccgtaa agaaaaataa gcacaagttt tatccggcct ttattcacat   3840
tcttgcccgc ctgatgaatg ctcatccgga attccgtatg gcaatgaaag acggtgagct   3900
ggtgatatgg gatagtgttc acccttgtta caccgttttc catgagcaaa ctgaaacgtt   3960
ttcatcgctc tggagtgaat accacgacga tttccggcag tttctacaca tatattcgca   4020
agatgtggcg tgttacggtg aaaacctggc ctatttccct aaagggttta ttgagaatat   4080
gtttttcgtc tcagccaatc cctgggtgag tttcaccagt tttgatttaa acgtggccaa   4140
tatggacaac ttcttcgccc ccgttttcac catgggcaaa tattatacgc aaggcgacaa   4200
ggtgctgatg ccgctggcga ttcaggttca tcatgccgtt tgtgatggct tccatgtcgg   4260
cagaatgctt aatgaattac aacagtactg cgatgagtgg cagggcgggg cgtaaaactt   4320
cggcggcgcc cgagcgtgaa cagcacgggc tgaccaacct gtgcgcgcgc ggcggctacg   4380
tcctggcgga agccgaaggg acgcggcagg tcacgctggt cgccacgggg cacgaggcga   4440
tactggcgct ggcggcacgc aaactgttga aggacgcagg ggttgcggcg gctgtcgtat   4500
cccttccatg ctgggaactg ttcgccgcgc aaaaaatgac gtatcgtgcc gccgtgctgg   4560
gaacggcacc ccggatcggc attgaagccg cgtcagggtt tggatgggaa cgctggcttg   4620
ggacagacgg gctgtttgtt ggcattgacg ggttcgggac ggccgccccg gaccagccgg   4680
acagcgcgac tgacatcacg ccggaacgga tctgccgcga cgcgctgcgt ctggtccgtc   4740
ccctgtccga taccctgact gaaccggcgg gaggaaacgg cgcgccgccc gggatgacat   4800
cggccgatgt cagtgtgtga aatgtcagac cttacggaga aaataagaaa tcggacgagc   4860
tattgatgtc agaggttcag tcgccagtac ccgcggagag taggctagac cgcttttcca   4920
acaagatact gtcactgcgt ggggccaact atatagttgg agcgctgggg ctttgtgcac   4980
ttatcgccgc aaccacggtt acgctgtcca ttaatgagca gctgattgtg gcacttgtgt   5040
```

gtgtgctcgt ctttttcatt gtcgggcggg gcaagagccg gcgtacccag atctttctcg 5100
aggtgctctc ggcgctggtt tccctgcgtt acctgacatg gcgcctgacc gaaacgctgg 5160
acttcgacac atggattcag ggcgggctgg gtgtgaccct gctcatcgcc gagctgtatg 5220
ccctgtacat gctgtttctc agctatttcc agacaatcca gccgcttcat cgcacgccgc 5280
tccccctgcc ggacaatgtt gatgactggc ccaccgtcga tatcttcatc ccgacctatg 5340
atgaacagct gagcatcgtg cgcctgaccg tgctgggcgc gctgggtatc gactggccac 5400
ccgataaagt gaatgtctat atccttgatg atggcgtgcg cccggaattc gaacagtttg 5460
ccagggaatg tggttccctt tacatcgggc gcgtggacag ttcgcacgcc aaggcgggta 5520
acctaaacca cgccattaag cagacaagcg gcgattacat cctcatcctg gattgtgacc 5580
atattccgac acgcgcgttc ctgcagatcg cgatgggctg gatggtcgcc gaccgcaaga 5640
ttgccctgat gcagacgccg catcacttct actcccccga tccgttccag cgtaacctcg 5700
ccgtgggata tcgcaccccg ccggaaggca acctgttcta cggcgtcatt caggatggta 5760
acgacttctg gga 5773

<210> SEQ ID NO 21
<211> LENGTH: 40
<212> TYPE: DNA
<213> ORGANISM: Artificial Sequence
<220> FEATURE:
<223> OTHER INFORMATION: Synthetic bcs_m_F

<400> SEQUENCE: 21
gtacccgcgg agagtagatt ggaccgcttt tccaacaaga 40

<210> SEQ ID NO 22
<211> LENGTH: 40
<212> TYPE: DNA
<213> ORGANISM: Artificial Sequence
<220> FEATURE:
<223> OTHER INFORMATION: Synthetic bcs_m_R

<400> SEQUENCE: 22
tcttgttgga aaagcggtcc aatctactct ccgcgggtac 40

<210> SEQ ID NO 23
<211> LENGTH: 5773
<212> TYPE: DNA
<213> ORGANISM: Artificial Sequence
<220> FEATURE:
<223> OTHER INFORMATION: Synthetic pUC19_bcsA_m plasmid

<400> SEQUENCE: 23
gaattcactg gccgtcgttt tacaacgtcg tgactgggaa aaccctggcg ttacccaact 60
taatcgcctt gcagcacatc cccctttcgc cagctggcgt aatagcgaag aggcccgcac 120
cgatcgccct tcccaacagt tgcgcagcct gaatggcgaa tggcgcctga tgcggtattt 180
tctccttacg catctgtgcg gtatttcaca ccgcatatgg tgcactctca gtacaatctg 240
ctctgatgcc gcatagttaa gccagccccg acacccgcca acacccgctg acgcgccctg 300
acgggcttgt ctgctcccgg catccgctta cagacaagct gtgaccgtct ccgggagctg 360
catgtgtcag aggttttcac cgtcatcacc gaaacgcgcg agacgaaagg gcctcgtgat 420
acgcctattt ttataggtta atgtcatgat aataatggtt tcttagacgt caggtggcac 480
ttttcgggga aatgtgcgcg gaacccctat ttgtttattt ttctaaatac attcaaatat 540

-continued

```
gtatccgctc atgagacaat aaccctgata aatgcttcaa taatattgaa aaaggaagag    600
tatgagtatt caacatttcc gtgtcgccct tattcccttt tttgcggcat tttgccttcc    660
tgtttttgct cacccagaaa cgctggtgaa agtaaaagat gctgaagatc agttgggtgc    720
acgagtgggt tacatcgaac tggatctcaa cagcggtaag atccttgaga gttttcgccc    780
cgaagaacgt tttccaatga tgagcacttt taaagttctg ctatgtggcg cggtattatc    840
ccgtattgac gccgggcaag agcaactcgg tcgccgcata cactattctc agaatgactt    900
ggttgagtac tcaccagtca cagaaaagca tcttacggat ggcatgacag taagagaatt    960
atgcagtgct gccataacca tgagtgataa cactgcggcc aacttacttc tgacaacgat   1020
cggaggaccg aaggagctaa ccgctttttt gcacaacatg ggggatcatg taactcgcct   1080
tgatcgttgg gaaccggagc tgaatgaagc cataccaaac gacgagcgtg acaccacgat   1140
gcctgtagca atggcaacaa cgttgcgcaa actattaact ggcgaactac ttactctagc   1200
ttcccggcaa caattaatag actggatgga ggcggataaa gttgcaggac cacttctgcg   1260
ctcggccctt ccggctggct ggtttattgc tgataaatct ggagccggtg agcgtgggtc   1320
tcgcggtatc attgcagcac tggggccaga tggtaagccc tcccgtatcg tagttatcta   1380
cacgacgggg agtcaggcaa ctatggatga acgaaataga cagatcgctg agataggtgc   1440
ctcactgatt aagcattggt aactgtcaga ccaagtttac tcatatatac tttagattga   1500
tttaaaactt catttttaat ttaaaaggat ctaggtgaag atcctttttg ataatctcat   1560
gaccaaaatc ccttaacgtg agttttcgtt ccactgagcg tcagaccccg tagaaaagat   1620
caaaggatct tcttgagatc ctttttttct gcgcgtaatc tgctgcttgc aaacaaaaaa   1680
accaccgcta ccagcggtgg tttgtttgcc ggatcaagag ctaccaactc tttttccgaa   1740
ggtaactggc ttcagcagag cgcagatacc aaatactgtt cttctagtgt agccgtagtt   1800
aggccaccac ttcaagaact ctgtagcacc gcctacatac ctcgctctgc taatcctgtt   1860
accagtggct gctgccagtg gcgataagtc gtgtcttacc gggttggact caagacgata   1920
gttaccggat aaggcgcagc ggtcgggctg aacggggggt tcgtgcacac agcccagctt   1980
ggagcgaacg acctacaccg aactgagata cctacagcgt gagctatgag aaagcgccac   2040
gcttcccgaa gggagaaagg cggacaggta tccggtaagc ggcagggtcg gaacaggaga   2100
gcgcacgagg gagcttccag ggggaaacgc ctggtatctt tatagtcctg tcgggtttcg   2160
ccacctctga cttgagcgtc gatttttgtg atgctcgtca ggggggcgga gcctatggaa   2220
aaacgccagc aacgcggcct ttttacggtt cctggccttt tgctggcctt ttgctcacat   2280
gttctttcct gcgttatccc ctgattctgt ggataaccgt attaccgcct ttgagtgagc   2340
tgataccgct cgccgcagcc gaacgaccga gcgcagcgag tcagtgagcg aggaagcgga   2400
agagcgccca atacgcaaac cgcctctccc cgcgcgttgg ccgattcatt aatgcagctg   2460
gcacgacagg tttcccgact ggaaagcggg cagtgagcgc aacgcaatta atgtgagtta   2520
gctcactcat taggcacccc aggctttaca ctttatgctt ccggctcgta tgttgtgtgg   2580
aattgtgagc ggataacaat ttcacacagg aaacagctat gaccatgatt acgccaagct   2640
ttaacgactc cggcatatga gcccgcgccg cagccagctc cggcccctgt tgtgcaggcc   2700
gcgccgtcgc agtcggcagc agccgtgacg ccatcggccc ctgaagtgcc gccccagccc   2760
gtaaggcagg agcggccggt agtgccgcca gtgccgccca ggcctgcggt gtcttccttc   2820
atggcgccgc gtcctgcggc tccggctttt ggcacgacag cgtcagccac gccccctgtt   2880
gcggtggagg actgggcgcc cgtgcccaag gcccagcagc agcgtgggca gcgtttgaca   2940
```

-continued

```
ggaccaggct tctttttcgg cgccggaagc gaacgggcgc ccgcagcaag gctgttccag   3000
tcagcaccgg tgtcccggcc tgtttcaaaa cctgtttcca aggtgaccac aatgaccaaa   3060
gttgacaaga tttccccgaa tgacagtcag gctgggcgtc ccgtgccgac cgacaattcc   3120
ccgaccctga ccgaagtgtt catgaccctt ggcggtcggg ccacggaccg gttggtgccc   3180
aagcccagcc tgcgcgatgc cctgttgcgc aagcgtgaag acgcgaacgg cgactcctga   3240
aaccgtgccg gggtgacct gctcccggca tgccagagga aggaagggga aaggttttcc   3300
ccgccccgca tccgctgcgg gccgaaaggc gacatgacgg accgaatgcg tctgacggtt   3360
ttcttttgaa tatataacga cctgttttac cagtatttat tatcggacga gctattgggc   3420
tgtgcaggtc gtaaatcact gcataattcg tgtcgctcaa ggcgcactcc cgttctggat   3480
aatgtttttt gcgccgacat cataacggtt ctggcaaata ttctgaaatg agctgttgac   3540
aattaatcat cggctcgtat aatgtgtgga attgtgagcg gataacaatt tcacacagga   3600
aacatagatc tcccgggtac cgagctctct agaaagaagg agggacgagc tattgatgga   3660
gaaaaaaatc actggatata ccaccgttga tatatcccaa tggcatcgta aagaacattt   3720
tgaggcattt cagtcagttg ctcaatgtac ctataaccag accgttcagc tggatattac   3780
ggccttttta aagaccgtaa agaaaaataa gcacaagttt tatccggcct ttattcacat   3840
tcttgcccgc ctgatgaatg ctcatccgga attccgtatg gcaatgaaag acggtgagct   3900
ggtgatatgg gatagtgttc acccttgtta caccgttttc catgagcaaa ctgaaacgtt   3960
ttcatcgctc tggagtgaat accacgacga tttccggcag tttctacaca tatattcgca   4020
agatgtggcg tgttacggtg aaaacctggc ctatttccct aaagggttta ttgagaatat   4080
gtttttcgtc tcagccaatc cctgggtgag tttcaccagt tttgatttaa acgtggccaa   4140
tatggacaac ttcttcgccc ccgttttcac catgggcaaa tattatacgc aaggcgacaa   4200
ggtgctgatg ccgctggcga ttcaggttca tcatgccgtt tgtgatggct tccatgtcgg   4260
cagaatgctt aatgaattac aacagtactg cgatgagtgg cagggcgggg cgtaaaactt   4320
cggcggcgcc cgagcgtgaa cagcacgggc tgaccaacct gtgcgcgcgc ggcggctacg   4380
tcctggcgga agccgaaggg acgcggcagg tcacgctggt cgccacgggg cacgaggcga   4440
tactggcgct ggcggcacgc aaactgttga aggacgcagg ggttgcggcg gctgtcgtat   4500
cccttccatg ctgggaactg ttcgccgcgc aaaaaatgac gtatcgtgcc gccgtgctgg   4560
gaacggcacc ccggatcggc attgaagccg cgtcagggtt tggatgggaa cgctggcttg   4620
ggacagacgg gctgtttgtt ggcattgacg ggttcgggac ggccgccccg gaccagccgg   4680
acagcgcgac tgacatcacg ccggaacgga tctgccgcga cgcgctgcgt ctggtccgtc   4740
ccctgtccga taccctgact gaaccggcgg gaggaaacgg cgcgccgccc gggatgacat   4800
cggccgatgt cagtgtgtga aatgtcagac cttacggaga aaataagaaa tcggacgagc   4860
tattgatgtc agaggttcag tcgccagtac ccgcggagag tagattggac cgcttttcca   4920
acaagatact gtcactgcgt ggggccaact atatagttgg agcgctgggg ctttgtgcac   4980
ttatcgccgc aaccacggtt acgctgtcca ttaatgagca gctgattgtg gcacttgtgt   5040
gtgtgctcgt ctttttcatt gtcgggcggg gcaagagccg gcgtacccag atctttctcg   5100
aggtgctctc ggcgctggtt tccctgcgtt acctgacatg gcgcctgacc gaaacgctgg   5160
acttcgacac atggattcag ggcgggctgg gtgtgaccct gctcatcgcc gagctgtatg   5220
ccctgtacat gctgtttctc agctatttcc agacaatcca gccgcttcat cgcacgccgc   5280
```

tccccctgcc ggacaatgtt gatgactggc ccaccgtcga tatcttcatc ccgacctatg 5340
atgaacagct gagcatcgtg cgcctgaccg tgctgggcgc gctgggtatc gactggccac 5400
ccgataaagt gaatgtctat atccttgatg atggcgtgcg cccggaattc gaacagtttg 5460
ccagggaatg tggttccctt tacatcgggc gcgtggacag ttcgcacgcc aaggcgggta 5520
acctaaacca cgccattaag cagacaagcg gcgattacat cctcatcctg gattgtgacc 5580
atattccgac acgcgcgttc ctgcagatcg cgatgggctg gatggtcgcc gaccgcaaga 5640
ttgccctgat gcagacgccg catcacttct actcccccga tccgttccag cgtaacctcg 5700
ccgtgggata tcgcaccccg ccggaaggca acctgttcta cggcgtcatt caggatggta 5760
acgacttctg gga 5773

<210> SEQ ID NO 24
<211> LENGTH: 20
<212> TYPE: DNA
<213> ORGANISM: Artificial Sequence
<220> FEATURE:
<223> OTHER INFORMATION: Synthetic bcsA_F

<400> SEQUENCE: 24
atgtcagagg ttcagtcgcc 20

<210> SEQ ID NO 25
<211> LENGTH: 21
<212> TYPE: DNA
<213> ORGANISM: Artificial Sequence
<220> FEATURE:
<223> OTHER INFORMATION: Synthetic bcsA_R

<400> SEQUENCE: 25
gcgttatcca caaccgcatc a 21

<210> SEQ ID NO 26
<211> LENGTH: 2265
<212> TYPE: DNA
<213> ORGANISM: Komagataeibacter xylinus

<400> SEQUENCE: 26
atgtcagagg ttcagtcgcc agtacccgcg gagagtaggc tagaccgctt ttccaacaag 60
atactgtcac tgcgtggggc caactatata gttggagcgc tggggctttg tgcacttatc 120
gccgcaacca cggttacgct gtccattaat gagcagctga ttgtggcact tgtgtgtgtg 180
ctcgtctttt tcattgtcgg gcggggcaag agccggcgta cccagatctt tctcgaggtg 240
ctctcggcgc tggtttccct gcgttacctg acatggcgcc tgaccgaaac gctggacttc 300
gacacatgga ttcagggcgg gctgggtgtg accctgctca tcgccgagct gtatgccctg 360
tacatgctgt ttctcagcta tttccagaca atccagccgc ttcatcgcac gccgctcccc 420
ctgccggaca atgttgatga ctggcccacc gtcgatatct tcatcccgac ctatgatgaa 480
cagctgagca tcgtgcgcct gaccgtgctg ggcgcgctgg gtatcgactg gccacccgat 540
aaagtgaatg tctatatcct tgatgatggc gtgcgcccgg aattcgaaca gtttgccagg 600
gaatgtggtt ccctttacat cgggcgcgtg gacagttcgc acgccaaggc gggtaaccta 660
aaccacgcca ttaagcagac aagcggcgat tacatcctca tcctggattg tgaccatatt 720
ccgacacgcg cgttcctgca gatcgcgatg ggctggatgg tcgccgaccg caagattgcc 780
ctgatgcaga cgccgcatca cttctactcc cccgatccgt tccagcgtaa cctcgccgtg 840
ggatatcgca ccccgccgga aggcaacctg ttctacggcg tcattcagga tggtaacgac 900

-continued

```
ttctgggatg ccaccttctt ctgcggctcg tgcgccatcc tgcgccgtga ggcgattgaa    960

tcgatcggcg gcttcgcggt tgaaaccgtg acggaagatg cccataccgc cctgcgcatg   1020

cagcgccgtg gctggtccac tgcctacttg cgcattcctg tggccagtgg cctggctacc   1080

gagcgcctga caacccatat cggccagcgc atgcgctggg cgcgcggcat gatccagatc   1140

ttccgcgtgg ataatccgat gcttgggtcg gggctgaagc ttggccagcg gctgtgctac   1200

ctctcggcta tgacgtcgtt cttcttcgcc attccgcgcg tcatcttcct cgcctcgccg   1260

ctggcgttcc tgttcgcggg ccagaacatc atcgccgcct cgccgctggc cgttctggcc   1320

tacgccattc cgcatatgtt ccactccatc gcgaccgccg ccaaggtaaa caagggctgg   1380

cgctactcgt tctggagtga agtgtacgaa accaccatgg cgctgttcct ggtgcgcgtg   1440

accatcatca ccatgatgtt cccctctaag ggcaagttca acgtgacgga aaagggtggg   1500

gtgctggagg aggaagagtt cgatcttggc gcgacctacc ccaacatcat ctttgccgtc   1560

atcatggcgc ttggcctgct gatcggcctg ttcgaactga tcttccactt cagccagctt   1620

gatggcatcg ccatgcgcgc ctacgcgctg aactgcatct gggccgcgat cagtctcatc   1680

atccttctgg ctgccattgc ggtggggcgt gaaaccaaac aggtccgtta cagccatcgt   1740

atcgatgcgc atatcccggt aacggtttat gaagcgccgg tcgcggggca gcccaatacc   1800

taccataatg cgacaccggg catgacccag gatgtttcca tgggtggtgt tgccgtgcat   1860

atgccctggc ccgatatcgg ctcggggccg gtcaagacac gtatccatgc cgtgctcgat   1920

ggcgaggaga tcgatattcc cgccaccatg ctgcgctgca agaatggcaa ggccgtgttc   1980

acatgggaca ataatgacct tgatacggaa cgcgatatcg tccgcttcgt gttcgggcgg   2040

gccgatgcct ggctgcaatg gaataattat gaggatgaca ggccgctacg cagcctgtgg   2100

agcctgctgc tcagcattaa ggcgctgttc cgcaaaaaag gcaaaatgat ggccaatagt   2160

cgtccaacaa aaaaaccacg tgcactaccg gttgagcgca gggagcccac aaccatccag   2220

agtggacaga cacaggaagg aaagatcagc cgtgcggcct cgtga                   2265
```

<210> SEQ ID NO 27
<211> LENGTH: 18
<212> TYPE: DNA
<213> ORGANISM: Artificial Sequence
<220> FEATURE:
<223> OTHER INFORMATION: Synthetic Recognitin site

<400> SEQUENCE: 27
gagagtaggc tagaccgc 18

<210> SEQ ID NO 28
<211> LENGTH: 18
<212> TYPE: DNA
<213> ORGANISM: Artificial Sequence
<220> FEATURE:
<223> OTHER INFORMATION: Synthetic Modified recognitin site

<400> SEQUENCE: 28
gagagtagat tggaccgc 18

<210> SEQ ID NO 29
<211> LENGTH: 6
<212> TYPE: PRT
<213> ORGANISM: Artificial Sequence
<220> FEATURE:
<223> OTHER INFORMATION: Synthetic Recognitin site -continued

<400> SEQUENCE: 29

```
Glu Ser Arg Leu Asp Arg
1               5
```